(12) United States Patent
Nakashima et al.

(10) Patent No.: US 10,610,554 B2
(45) Date of Patent: Apr. 7, 2020

(54) ONCOLYTIC EXPRESSION VECTOR COMPRISING A NUCLEIC ACID COMPRISING A NUCLEOTIDE SEQUENCE ENCODING GADD34

(71) Applicants: THE BRIGHAM AND WOMEN'S HOSPITAL, INC., Boston, MA (US); Ohio State Innovation Foundation, Columbus, OH (US)

(72) Inventors: Hiroshi Nakashima, Framingham, MA (US); Ennio Antonio Chiocca, Powell, OH (US)

(73) Assignees: The Brigham and Women's Hospital, Inc., Boston, MA (US); Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/262,442

(22) Filed: Jan. 30, 2019

(65) Prior Publication Data
US 2019/0160123 A1 May 30, 2019

Related U.S. Application Data

(66) Division of application No. 14/442,632, filed as application No. PCT/US2013/070087 on Nov. 14, 2013, now Pat. No. 10,232,002, Substitute for application No. 61/726,318, filed on Nov. 14, 2012.

(51) Int. Cl.
| | |
|---|---|
| *A61K 35/768* | (2015.01) |
| *C12N 15/86* | (2006.01) |
| *C12N 7/00* | (2006.01) |
| *A61K 35/763* | (2015.01) |
| *A61K 48/00* | (2006.01) |
| *C07K 14/47* | (2006.01) |
| *A61K 38/17* | (2006.01) |

(52) U.S. Cl.
CPC .......... *A61K 35/768* (2013.01); *A61K 35/763* (2013.01); *A61K 38/1709* (2013.01); *A61K 48/005* (2013.01); *C07K 14/47* (2013.01); *C12N 7/00* (2013.01); *C12N 15/86* (2013.01); *A61K 48/00* (2013.01); *C12N 2710/16043* (2013.01); *C12N 2710/16632* (2013.01); *C12N 2710/16643* (2013.01); *C12N 2710/16652* (2013.01); *C12N 2800/204* (2013.01); *C12N 2800/30* (2013.01); *C12N 2800/50* (2013.01); *C12N 2830/008* (2013.01)

(58) Field of Classification Search
CPC ............ C12N 7/00; C12N 2710/16043; C12N 2710/16632; C12N 2710/16643; C12N 2710/16652; C12N 2800/204; C12N 2800/03; C12N 2800/50; C12N 2830/008; C12N 15/86; A61K 35/763; A61K 48/005; A61K 35/768; A61K 38/1709; A61K 48/00; C07K 14/47
See application file for complete search history.

(56) References Cited

U.S. PATENT DOCUMENTS

2010/0272686 A1  10/2010  Kaur et al.

OTHER PUBLICATIONS

Bennett et al., "Up-regulation of GADD34 mediates the synergistic anticancer activity of mitomycin C and a γ134. 5 deleted oncolytic herpes virus (G207)", The FASEB Journal 18(9):1001-1003 (2004).
Carson et al., "Oncolytic Herpes Simplex Virus 1 (HSV-1) Vectors: Increasing Treatment Efficacy and Range Through Strategic Virus Design", Drugs Future 35(3):183-195 (2010).
Database EMBL-Bank, AY891966 Mar. 25, 2005.
Hollander et al., "Mammalian GADD34, an Apoptosis-and DNA Damage-inducible Gene", Journal of Biological Chemistry 272(21):13731-13737 (1997).
Kim et al., "Combination of mutated herpes simplex virus type 1 (G207 virus) with radiation for the treatment of squamous cell carcinoma of the head and neck", European Journal of Cancer 41:313-322 (2005).
McCabe et al., "GADD34 gene restores virulence in viral vector used in experimental stroke study", J Cereb Blood Flow Metab. 28(4):747-751 (2008).
Mikami et al., "N-terminally truncated GABB34 proteins are convenient translation enhancers in a human cell-derived in vitro protein synthesis system", Biotechnol Lett 32: 897-902 (2010).
Yang et al., "Lab-Experimental (Pre-Clinical) Therapeutics and Pharmacology", Neuro-Oncology 14: vi25-vi37 (2012).
Nakashima et al. "ET-56. Development of an efficient and safe oncolytic HSV-1 vector for glioblastoma therapy." Neuro-Oncology Lab-Experimental (pre-clinical) therapeutics and pharmacology 14(suppl_6): vi25-v137 https://doi.org/10.1093/neuonc/nos222 (2012).

*Primary Examiner* — Titilayo Moloye
(74) *Attorney, Agent, or Firm* — Nixon Peabody LLP

(57) ABSTRACT

Malignant tumors that are resistant to conventional therapies represent significant therapeutic challenges. An embodiment of the present invention provides an oncolytic virus capable of killing target cells, such as tumor cells. In various embodiments presented herein, the oncolytic viruses described herein are suitable for treatment of several types of cancer, including glioblastoma.

7 Claims, 22 Drawing Sheets
Specification includes a Sequence Listing.

| Virus | Dm (MOI) | m | r |
|---|---|---|---|
| rHSVQ1 | 0.27 | 0.81791 +/- 0.118724 | 0.96035 |
| rQNes34.5 | 0.0147 | 0.72936 +/- 0.088548 | 0.95851 |
| NG34 | 0.00779 | 0.60942 +/- 0.032661 | 0.99149 |
| NG34C | 0.0233 | 0.97500 +/- 0.101319 | 0.97405 |
| hrR3 | 0.00375 | 1.73104 +/- 0.081637 | 0.99778 |
| Strain F | 0.00311 | 0.70743 +/- 0.060976 | 0.98193 |

U87ΔEGFR cell line (TMZ ED$_{30}$)

| rHSVQ1 (MOI) | OV (%) | OV+TMZ (%) | CI* | Symbol | Description |
|---|---|---|---|---|---|
| 1.0 | 67.58 | 76.95 | 0.946 | ± | Nearly additive |
| 0.33 | 69.86 | 74.70 | 0.459 | +++ | Synergism |
| 0.11 | 40.08 | 57.71 | 0.565 | +++ | Synergism |
| 0.037 | 7.03 | 34.51 | 1.008 | ± | Nearly additive |

| rQNes34.5 (MOI) | OV (%) | OV+TMZ (%) | CI* | Symbol | Description |
|---|---|---|---|---|---|
| 0.33 | 76.8 | 84.7 | 0.344 | +++ | Synergism |
| 0.11 | 64.4 | 76.5 | 0.363 | +++ | Synergism |
| 0.037 | 39.6 | 64.4 | 0.525 | +++ | Synergism |
| 0.012 | 24.3 | 60.0 | 0.558 | +++ | Synergism |
| 0.0041 | 12.5 | 57 | 0.607 | +++ | Synergism |

*CI: combination index

FIG. 13A

| NG34C (MOI) | OV (%) | OV+TMZ (%) | CI* | Symbol | Description |
|---|---|---|---|---|---|
| 0.33 | 89.71 | 99.22 | 0.103 | ++++ | Strong Synergism |
| 0.11 | 83.79 | 95.97 | 0.204 | ++++ | Strong Synergism |
| 0.037 | 61.05 | 89.03 | 0.240 | ++++ | Strong Synergism |
| 0.012 | 58.01 | 58.03 | 0.668 | +++ | Synergism |
| 0.0041 | 9.08 | 41.16 | 0.804 | ++ | Moderate Synergism |
| 0.00137 | 8.28 | 30.88 | 0.974 | ± | Nearly additive |

| NG34 (MOI) | OV (%) | OV+TMZ (%) | CI* | Symbol | Description |
|---|---|---|---|---|---|
| 1.0 | 85.7 | 86.6 | 0.752 | ++ | Moderate Synergism |
| 0.33 | 76.8 | 84.7 | 0.389 | +++ | Synergism |
| 0.11 | 64.4 | 84.8 | 0.196 | ++++ | Strong Synergism |
| 0.037 | 39.6 | 72.1 | 0.371 | +++ | Synergism |
| 0.012 | 24.3 | 76.1 | 0.228 | ++++ | Strong Synergism |
| 0.0041 | 12.5 | 64.0 | 0.433 | +++ | Synergism |

SEQUENCE LISTING

```
<160> NUMBER OF SEQ ID NOS: 8

<210> SEQ ID NO 1
<211> LENGTH: 2022
<212> TYPE: DNA
<213> ORGANISM: Homo sapiens

<400> SEQUENCE: 1
atggccccag gccaagcacc ccatcaggct accccgtgga gggatgccca cccttcttc       60 ctcctgtccc cagtgatggg cctcctcagc cgcgcctgga gccgcctgag gggcctggga     120
cctctagagc cctggctggt ggaagcagta aaaggagcag ctctggtaga agctggcctg     180
gagggagaag ctaggactcc tctggcaatc ccccatacccc cttggggcag acgccctgaa    240
gaggaggctg aagacagtgg aggccctgga gaggacagag aaacactggg gctgaaaacc    300
```

```
agcagttccc ttcctgaagc ctggggactt ttggatgatg atgatggcat gtatggtgag    360
cgagaggcaa ccagtgtccc tagagggcag ggaagtcaat ttgcagatgg ccagcgtgct    420
cccctgtctc ccagccttct gataaggaca ctgcaaggtt ctgataagaa cccaggggag    480
gagaaagccg aggaagaggg agttgctgaa gaggaggag ttaacaagtt ctcttatcca     540
ccatcacacc gggagtgttg tccagccgtg gaggaggagg acgatgaaga agctgtaaag    600
aaagaagctc acagaacctc tacttctgcc ttgtctccag gatccaagcc cagcacttgg    660
gtgtcttgcc caggggagga agagaatcaa gccacggagg ataaaagaac agaaagaagt    720
aaaggagcca ggaagacctc cgtgtccccc cgatcttcag gctccgaccc caggtcctgg    780
gagtatcgtt caggagaggc gtccgaggag aaggaggaaa aggcacacaa agaaactggg    840
aaaggagaag ctgccccagg gccgcaatcc tcagccccag cccagaggcc ccagctcaag    900
tcctggtggt gccaacccag tgatgaagag gagggtgagg tcaaggcttt ggggcagct    960 gagaaggatg agaagctga gtgtcctccc tgcatccccc caccaagtgc cttcctgaag    1020
gcctgggtgt attggccagg agaggacaca gaggaagagg aagatgagga agaagatgag    1080
gacagtgact ctggatcaga tgaggaagag ggagaagctg aggcttcctc ttccactcct    1140
gctacaggtg tcttcttgaa gtcctgggtc tatcagccag gagaggacac agaggaggag    1200
gaagatgagg acagtgatac aggatcagcc gaggatgaaa gagaagctga gacttctgct    1260
tccacacccc ctgcaagtgc tttcttgaag gcctgggtgt atcggccagg agaggacacg    1320
gaggaggagg aagatgagga tgtggatagt gaggataagg aagatgattc agaagcagcc    1380
ttgggagaag ctgagtcaga cccacatccc tcccacccgg accagagggc ccacttcagg    1440
ggctggggat atcgacctgg aaaagagaca gaggaagagg aagctgctga ggactgggga    1500
gaagctgagc cctgcccctt ccgagtggcc atctatgtac ctggagagaa gccaccgcct    1560
ccctgggctc ctcctaggct gcccctccga ctgcaaaggc ggctcaagcg cccagaaacc    1620
cctactcatg atccggaccc tgagactccc ctaaaggcca gaaaggtgcg cttctccgag    1680
aaggtcactg tccatttcct ggctgtctgg gcagggccgg cccaggccgc ccgccagggc    1740
ccctgggagc agcttgctcg ggatcgcagc cgcttcgcac gccgcatcac ccaggcccag    1800
gaggagctga gccctgcct caccctgct gcccgggcca gagcctgggc acgcctcagg    1860
aacccacctt tagcccccat ccctgccctc acccagacct tgccttcctc ctctgtccct    1920
tcgtccccag tccagaccac gcccttgagc caagctgtgg ccacaccttc ccgctcgtct    1980
gctgctgcag cggctgccct ggacctcagt gggaggcgtg gc                       2022
```

<210> SEQ ID NO 2
<211> LENGTH: 1503
<212> TYPE: DNA
<213> ORGANISM: Homo sapiens

<400> SEQUENCE: 2

```
atgaacaagt tctcttatcc accatcacac cgggagtgtt gtccagccgt ggaggaggag     60
gacgatgaag aagctgtaaa gaaagaagct cacagaacct ctacttctgc cttgtctcca    120
ggatccaagc ccagcacttg ggtgtcttgc ccaggggagg aagagaatca agccacggag    180
gataaaagaa cagaaagaag taaggagcc aggaagacct ccgtgtcccc ccgatcttca     240
ggctccgacc ccaggtcctg ggagtatcgt tcaggagagg cgtccgagga aggaggaa      300 aaggcacaca agaaactggg aaaggagaa gctgccccag ggccgcaatc ctcagcccca    360
```

```
gcccagaggc cccagctcaa gtcctggtgg tgccaaccca gtgatgaaga ggagggtgag    420
gtcaaggctt tggggcagc tgagaaggat ggagaagctg agtgtcctcc ctgcatcccc     480
ccaccaagtg ccttcctgaa ggcctggtg tattggccag gagaggacac agaggaagag    540
gaagatgagg aagaagatga ggacagtgac tctggatcag atgaggaaga gggagaagct    600
gaggcttcct cttccactcc tgctacaggt gtcttcttga agtcctgggt ctatcagcca    660
ggagaggaca cagaggagga ggaagatgag gacagtgata caggatcagc cgaggatgaa    720
agagaagctg agacttctgc ttccacaccc cctgcaagtg ctttcttgaa ggcctgggtg    780
tatcggccag gagaggacac ggaggaggag gaagatgagg atgtggatag tgaggataag    840
gaagatgatt cagaagcagc cttgggagaa gctgagtcag acccacatcc ctcccacccg    900
gaccagaggg cccacttcag gggctgggga tatcgacctg gaaaagagac agaggaagag    960
gaagctgctg aggactgggg agaagctgag ccctgcccct tccgagtggc catctatgta   1020
cctggagaga agccaccgcc tccctgggct cctcctaggc tgccctccg actgcaaagg    1080 cggctcaagc gcccagaaac ccctactcat gatccggacc ctgagactcc cctaaaggcc   1140
agaaaggtgc gcttctccga aaggtcact gtccatttcc tggctgtctg gcagggccg    1200 gcccaggccg cccgccaggg cccctgggag cagcttgctc gggatcgcag ccgcttcgca   1260
cgccgcatca cccaggccca ggaggagctg agccctgcc tcacccctgc tgcccgggcc    1320
agagcctggg cacgcctcag gaacccacct ttagccccca tccctgccct cacccagacc   1380
ttgccttcct cctctgtccc ttcgtcccca gtccagacca cgcccttgag ccaagctgtg   1440
gccacacctt cccgctcgtc tgctgctgca gcggctgccc tggacctcag tgggaggcgt   1500
ggc                                                                 1503

<210> SEQ ID NO 3
<211> LENGTH: 1540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aaccctgaag agtttgtgat cctgagatga gggctttagc cccagtcagt cctctgaggg    60
gaagggtcca ggcagctctg aggaatgtaa ccactggcgt ttgaggtctg aaaaggattt   120
ggagaagggg agctgaattc atttgctttt gtctgttacc agctctgggg gcagagagag    180
agccatcccc tgggaacagc ctgagaattc ccacttcccc tgaggagccc tcccttctta    240
ggccctccag atggtagtgt ggacaaaagg caataattag catgagaatc ggcctccctc    300
ccagaggatg aggtcatcgg ccttggcctt ggtggggag gcggagactg atctgaggag    360
tctgatataa gtgttagcaa ttcatttggc cctgcctccg actgtgggaa tctgcatgtg    420
gggtctccct gtgtctcaaa tatggggttgg ctaagtatat atctgtgggt atatgactgt    480
gtggctttta tatgacaatg gtcacaatag agattgatcc tgcagtggca ggacatgcta    540
cctcagctgg agctgaccct atctccccac tccccaccag gactctgctg gaggctgaga    600
actctcggtt gcagacacct ggacgaggtt caggcttatc atatgactag tagatcctct    660
aggggcgatc gcgggtaccg agctccagga acatccaaac tgagcagccg ggtcccccc     720 cacccccac cccgccctc ccggcaactt tgagcctgtg ctgggacaga gcctctagtt     780
cctaaattag tccatgaggt cagaggcagc actgccattg taacgcgatt ggagaggatc    840
```

| | |
|---|---|
| acgtcaccgg acacgccccc aggcatctcc ctgggtctcc taaacttggc ggggagaagt | 900 |
| tttagccctt aagttttagc ctttaacccc catattcaga actgtgcgag ttggcgaaac | 960 |
| cccacaaatc acaacaaact gtacacaaca ccgagctaga ggtgatcttt cttgtccatt | 1020 |
| ccacacaggc cttagtaatg cgtcgccata gcaacagtgt cactagtagc accagcactt | 1080 |
| ccccacaccc tcccctcag gaatccgtac tctccagtga accccagaaa cctctggaga | 1140 |
| gttctggaca agggcggaac ccacaactcc gattactcaa gggaggcggg gaagctccac | 1200 |
| cagacgcgaa actgctggaa gattcctggc cccaaggcct cctccggctc gctgattggc | 1260 |
| ccagcggaga gtgggcgggg ccggtgaaga ctccttaaag gcgcagggcg gcgagcaggt | 1320 |
| caccagacgc tgacagctac tcagaaccaa atctggttcc atccagagac aagcgaagac | 1380 |
| aagagaagca gagcgagcgg cgcgttcccg atcctcggcc aggaccagcc ttccccagag | 1440 |
| catccctgcc gcggagcgca accttcccag gagcatccct gccgcggagc gcaactttcc | 1500 |
| ccggagcatc cacgccgcgg agcgcagcct tccagaagca | 1540 |

```
<210> SEQ ID NO 4
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
```

| | |
|---|---|
| aaccctgaag agtttgtgat cctgagatga gggctttagc cccagtcagt cctctgaggg | 60 |
| gaagggtcca ggcagctctg aggaatgtaa ccactggcgt tgaggtctg aaaaggattt | 120 |
| ggagaagggg agctgaattc atttgctttt gtctgttacc agctctgggg gcagagagag | 180 |
| agccatcccc tgggaacagc ctgagaattc ccacttcccc tgaggagccc tcccttctta | 240 |
| ggccctccag atggtagtgt ggacaaaagg caataattag catgagaatc ggcctccctc | 300 |
| ccagaggatg aggtcatcgg ccttggcctt gggtggggag gcggagactg atctgaggag | 360 |
| tctgatataa gtgttagcaa ttcatttggc cctgcctccg actgtgggaa tctgcatgtg | 420 |
| gggtctccct gtgtctcaaa tatggggttgg ctaagtatat atctgtgggt atatgactgt | 480 |
| gtggcttta tatgacaatg gtcacaatag agattgatcc tgcagtggca ggacatgcta | 540 |
| cctcagctgg agctgaccct atctccccac tccccaccag gactctgctg gaggctgaga | 600 |
| actctcggtt gcagacacct ggacgaggtt | 630 |

```
<210> SEQ ID NO 5
<211> LENGTH: 910
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

| | |
|---|---|
| caggcttatc atatgactag tagatcctct aggggcgatc gcgggtaccg agctccagga | 60 |
| acatccaaac tgagcagccg gggtcccccc caccccccac cccgcccctc ccggcaactt | 120 |
| tgagcctgtg ctgggacaga gcctctagtt cctaaattag tccatgaggt cagaggcagc | 180 |
| actgccattg taacgcgatt ggagaggatc acgtcaccgg acacgccccc aggcatctcc | 240 |
| ctgggtctcc taaacttggc ggggagaagt tttagccctt aagttttagc ctttaacccc | 300 |
| catattcaga actgtgcgag ttggcgaaac cccacaaatc acaacaaact gtacacaaca | 360 |

```
ccgagctaga ggtgatcttt cttgtccatt ccacacaggc cttagtaatg cgtcgccata    420
gcaacagtgt cactagtagc accagcactt ccccacaccc tcccctcag gaatccgtac    480 tctccagtga accccagaaa cctctggaga gttctggaca agggcggaac ccacaactcc    540
gattactcaa gggaggcggg gaagctccac cagacgcgaa actgctggaa gattcctggc    600
cccaaggcct cctccggctc gctgattggc ccagcggaga gtgggcgggg ccggtgaaga    660
ctccttaaag gcgcagggcg gcgagcaggt caccagacgc tgacagctac tcagaaccaa    720
atctggttcc atccagagac aagcgaagac aagagaagca gagcgagcgg cgcgttcccg    780
atcctcggcc aggaccagcc ttccccagag catccctgcc gcggagcgca accttcccag    840
gagcatccct gccgcggagc gcaactttcc ccggagcatc cacgccgcgg agcgcagcct    900
tccagaagca                                                          910

<210> SEQ ID NO 6
<211> LENGTH: 3058
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aaccctgaag agtttgtgat cctgagatga gggctttagc cccagtcagt cctctgaggg     60
gaagggtcca ggcagctctg aggaatgtaa ccactggcgt tgaggtctg aaaaggattt    120 ggagaagggg agctgaattc atttgctttt gtctgttacc agctctgggg gcagagagag    180
agccatcccc tgggaacagc ctgagaattc ccacttcccc tgaggagccc tcccttctta    240
ggccctccag atggtagtgt ggacaaaagg caataattag catgagaatc ggcctccctc    300
ccagaggatg aggtcatcgg ccttggcctt gggtggggag gcggagactg atctgaggag    360
tctgatataa gtgttagcaa ttcatttggc cctgcctccg actgtgggaa tctgcatgtg    420
gggtctccct gtgtctcaaa tatgggttgg ctaagtatat atctgtgggt atatgactgt    480 gtggcttta tatgacaatg gtcacaatag agattgatcc tgcagtggca ggacatgcta    540
cctcagctgg agctgaccct atctccccac tccccaccag gactctgctg gaggctgaga    600
actctcggtt gcagacacct ggacgaggtt caggcttatc atatgactag tagatccctct    660 aggggcgatc gcgggtaccg agctccagga acatccaaac tgagcagccg gggtcccccc    720
caccccccac cccgccctc ccggcaactt tgagcctgtg ctgggacaga gcctctagtt    780
cctaaattag tccatgaggt cagaggcagc actgccattg taacgcgatt ggagaggatc    840
acgtcaccgg acacgccccc aggcatctcc ctgggtctcc taaacttggc ggggagaagt    900
tttagccctt aagttttagc ctttaacccc catattcaga actgtgcgag ttggcgaaac    960
cccacaaatc acaacaaact gtacacaaca ccgagctaga ggtgatcttt cttgtccatt   1020
ccacacaggc cttagtaatg cgtcgccata gcaacagtgt cactagtagc accagcactt   1080
ccccacaccc tcccctcag gaatccgtac tctccagtga accccagaaa cctctggaga   1140
gttctggaca agggcggaac ccacaactcc gattactcaa gggaggcggg gaagctccac   1200
cagacgcgaa actgctggaa gattcctggc cccaaggcct cctccggctc gctgattggc   1260
ccagcggaga gtgggcgggg ccggtgaaga ctccttaaag gcgcagggcg gcgagcaggt   1320
caccagacgc tgacagctac tcagaaccaa atctggttcc atccagagac aagcgaagac   1380
aagagaagca gagcgagcgg cgcgttcccg atcctcggcc aggaccagcc ttccccagag   1440
```

-continued

```
catccctgcc gcggagcgca accttcccag gagcatccct gccgcggagc gcaactttcc    1500
ccggagcatc cacgccgcgg agcgcagcct tccagaagca gagcgcggcg ccatgaacaa    1560
gttctcttat ccaccatcac accgggagtg ttgtccagcc gtggaggagg aggacgatga    1620
agaagctgta aagaaagaag ctcacagaac ctctacttct gccttgtctc caggatccaa    1680
gcccagcact tgggtgtctt gccaggggga ggaagagaat caagccacgg aggataaaag    1740
aacagaaaga agtaaaggag ccaggaagac ctccgtgtcc ccccgatctt caggctccga    1800
ccccaggtcc tgggagtatc gttcaggaga ggcgtccgag gagaaggagg aaaaggcaca    1860
caaagaaact gggaaaggag aagctgcccc agggccgcaa tcctcagccc cagcccagag    1920
gccccagctc aagtcctggt ggtgccaacc cagtgatgaa gaggagggtg aggtcaaggc    1980
tttgggggca gctgagaagg atggagaagc tgagtgtcct ccctgcatcc ccccaccaag    2040
tgccttcctg aaggcctggg tgtattggcc aggagaggac acagaggaag aggaagatga    2100
ggaagaagat gaggacagtg actctggatc agatgaggaa gagggagaag ctgaggcttc    2160
ctcttccact cctgctacag gtgtcttctt gaagtcctgg gtctatcagc caggagagga    2220
cacagaggag gaggaagatg aggacagtga tacaggatca gccgaggatg aaagagaagc    2280
tgagacttct gcttccacac cccctgcaag tgctttcttg aaggcctggg tgtatcggcc    2340
aggagaggac acgaggagg aggaagatga ggatgtggat agtgaggata aggaagatga    2400
ttcagaagca gccttgggag aagctgagtc agacccacat ccctcccacc cggaccagag    2460
ggcccacttc aggggctggg gatatcgacc tggaaaagag acagaggaag aggaagctgc    2520
tgaggactgg ggagaagctg agccctgccc cttccgagtg gccatctatg tacctggaga    2580
gaagccaccg cctccctggg ctcctcctag gctgccccct cgactgcaaa ggcggctcaa    2640
gcgcccagaa acccctactc atgatccgga ccctgagact cccctaaagg ccagaaaggt    2700
gcgcttctcc gagaaggtca ctgtccattt cctggctgtc tgggcagggc cggcccaggc    2760
cgcccgccag ggcccctggg agcagcttgc tcgggatcgc agccgcttcg cacgccgcat    2820
cacccaggcc caggaggagc tgagcccctg cctcaccct gctgcccggg ccagagcctg    2880
ggcacgcctc aggaacccac ctttagcccc catccctgcc ctcacccaga ccttgccttc    2940
ctcctctgtc ccttcgtccc cagtccagac cacgcccttg agccaagctg tggccacacc    3000
ttcccgctcg tctgctgctg cagcggctgc cctggaccct agtgggaggc gtggctga    3058
```

<210> SEQ ID NO 7
<211> LENGTH: 4
<212> TYPE: PRT
<213> ORGANISM: Homo sapiens

<400> SEQUENCE: 7

Lys Val Arg Phe
1

<210> SEQ ID NO 8
<211> LENGTH: 4
<212> TYPE: PRT
<213> ORGANISM: Homo sapiens

<400> SEQUENCE: 8

Arg Ala Arg Ala
1

ONCOLYTIC EXPRESSION VECTOR COMPRISING A NUCLEIC ACID COMPRISING A NUCLEOTIDE SEQUENCE ENCODING GADD34

CROSS-REFERENCE TO RELATED APPLICATIONS

This application is a Divisional of U.S. patent application Ser. No. 14/442,632, filed May 13, 2015, which is a 35 U.S.C § 371 National Phase Entry Application of International Patent Application PCT/US2013/070087, filed on Nov. 14, 2013, which claims the benefit under 35 U.S.C. § 119(e) of U.S. Provisional Patent Application No. 61/726,318, filed on Nov. 14, 2012, the contents of each of which are incorporated herein by reference in their entirety.

STATEMENT REGARDING FEDERALLY-SPONSORED RESEARCH

This invention was made with government support under R21NS0632901, 1P01CA163205, and P01CA069246 awarded by National Institutes of Health. The government has certain rights in the invention.

FIELD OF INVENTION

The present invention is directed to the fields of virology, cancer biology, and medicine. More particularly, it concerns compositions and methods of treating cancer of the brain in a patient using oncolytic herpes simplex virus 1 (HSV-1) armed with therapeutic genes.

SEQUENCE LISTING

The instant application contains a Sequence Listing which has been submitted electronically in ASCII format and is hereby incorporated by reference in its entirety. Said ASCII copy, created on Nov. 14, 2013, is named 043214-076071-PCT_SL.txt and is 14,073 bytes in size.

BACKGROUND

Malignant tumors that are intrinsically resistant to conventional therapies represent significant therapeutic challenges. Such malignant tumors include, but are not limited to malignant gliomas and recurrent systemic solid tumors such as lung cancer. Malignant gliomas are the most abundant primary brain tumors, having an annual incidence of 6.4 cases per 100,000 (CBTRUS, 2002-2003). These neurologically devastating tumors are the most common subtype of primary brain tumors and are one of the deadliest human cancers. In the most aggressive cancer manifestation, glioblastoma multiforme (GBM), median survival duration for patients is 14 months, despite maximum treatment efforts. A prototypic disease, malignant glioma is inherently resistant to current treatment regimens. In fact, in approximately ⅓ of patients with GBM the tumor will continue to grow despite treatment with radiation and chemotherapy. Median survival even with aggressive treatment including surgery, radiation, and chemotherapy is less than 1 year (Schiffer, 1998). Because few good treatment options are available for many of these refractory tumors, the exploration of novel and innovative therapeutic approaches is important.

Gene therapy is a promising treatment for tumors, including gliomas, and the identification of genetic abnormalities contributing to malignancies is providing important information to aid in the design of gene therapies. Genetic abnormalities indicated in the progression of tumors include the inactivation of tumor suppressor genes and the overexpression of numerous growth factors and oncogenes. Tumor treatment may be accomplished by supplying a polynucleotide encoding a therapeutic polypeptide or other therapeutic that targets the mutations and resulting aberrant physiologies of tumors. It is these mutations and aberrant physiologies that distinguish tumor cells from normal cells. A tumor-selective virus is an especially promising tool for gene therapy, and recent advances in the knowledge of how viruses replicate have been used to design tumor-selective oncolytic viruses.

In gliomas, several kinds of conditionally replication competent viruses have been shown to be useful in animal models, for example: reoviruses that can replicate selectively in tumors with an activated ras pathway (Coffey et al., 1998); genetically altered herpes simplex viruses (Martuza et al., 1991; Mineta et al., 1995; Andreanski et al., 1997), including those that can be activated by the different expression of proteins in normal and cancer cells (Chase et al., 1998); and mutant adenoviruses that are unable to express the E1B55 kDa protein and are used to treat p53-mutant tumors (Bischof et al., 1996; Heise et al., 1997; Freytag et al., 1998; Kim et al., 1998). Taken together, these reports confirm the relevance of oncolytic viruses (OVs) as anticancer agents. In all three systems, the goal is the intratumoral spread of the virus and the ability to selectively kill cancer cells. Along with directly killing the cancers cells, agents that can also influence the microenvironment surrounding the tumor may enhance the therapeutic effect of the OV.

Replication selective oncolytic viruses have shown great promise as anti-tumor agents for solid tumors. The viruses have been constructed genetically so that they are able to preferentially replicate within tumor cells, while being at least somewhat restricted in their ability to replicate in normal cells. The principal anti-tumor mechanism of oncolytic viruses is through a direct cytopathic effect as they propagate and spread from initially infected tumor cells to surrounding tumor cells, achieving a larger volume of distribution and anticancer effects. Oncolytic herpes simplex viruses (HSVs) were initially designed and constructed for the treatment of brain tumors. Subsequently, they have been found to be effective in a variety of other human solid tumors, including breast, prostate, lung, ovarian, colon and liver cancers. The safety of oncolytic HSVs has also been extensively tested in mice and primates, which are extremely sensitive to HSV.

HSV-1 based oncolytic viruses are particularly promising because of: (1) their ability to infect a wide variety of tumors; (2) their inherent cytolytic nature; (3) their well-characterized large genome (152 Kb) that provides ample opportunity for genetic manipulations wherein many of the non-essential genes can be replaced by therapeutic genes; (4) their ability to remain as episomes that avoid insertional mutagenesis in infected cells; and (5) the availability of anti-herpetic drugs to keep in check possible undesirable replication.

Despite encouraging preclinical studies, results from early clinical trials have suggested that most of the current versions of oncolytic viruses, although acceptably safe, may only have limited anti-tumor activity on their own. While not wishing to be bound by any one particular theory, one of the main reasons for the sub-optimal oncolytic efficacy is probably because viral gene deletions that confer tumor selectivity also result in reduced potency of the virus in tumors. For example, the complete elimination of endogenous γ34.5 function from HSV, one of the common approaches for the construction of oncolytic HSV, significantly reduces viral replication potential and therefore may compromise the ability of the virus to spread within the targeted tumors (Kramm et al., 1997).

Considering the limited effective treatment options available for certain types of cancer, including certain types of brain cancer, there remains a need in the art for improved oncolytic viruses.

SUMMARY OF THE INVENTION

In various embodiments, the invention teaches an oncolytic expression vector including a nucleic acid that includes a nucleotide sequence encoding a GADD34 protein, or a biologically active portion thereof, wherein said nucleotide sequence is operably linked to an expression control sequence. In certain embodiments, the vector is a modified herpes simplex virus. In some embodiments, the modified herpes simplex virus is a herpes simplex virus deficient for a $\gamma_1 34.5$ gene. In certain embodiments, the nucleotide sequence includes SEQ ID NO: 1 or a degenerate variant thereof. In various embodiments, the nucleotide sequence includes SEQ ID NO: 2 or a degenerate variant thereof. In some embodiments, the expression control sequence includes a nestin promoter or a biologically active portion thereof. In various embodiments, the expression control sequence includes SEQ ID NO: 3 or a degenerate variant thereof.

In various embodiments, the invention teaches a method of killing intracranial tumor cells in a subject. In some embodiments, the method includes introducing into the vicinity of the tumor cells an oncolytic expression vector, said oncolytic expression vector including a nucleic acid that includes a nucleotide sequence encoding GADD34, or a biologically active portion thereof, wherein said nucleotide sequence is operably linked to an expression control sequence. In certain embodiments, the oncolytic expression vector is a modified herpes virus. In some embodiments, the modified herpes virus is deficient for a $\gamma_1 34.5$ gene. In some embodiments, the nucleotide sequence includes SEQ ID NO: 1 or a degenerate variant thereof. In some embodiments, the nucleotide sequence includes SEQ ID NO: 2 or of a degenerate variant thereof. In certain embodiments, the expression control sequence includes a nestin promoter or a biologically active portion thereof. In certain embodiments, the expression control sequence includes SEQ ID NO: 3. In some embodiments, the method also includes the step of mixing a pharmacologically acceptable carrier with the oncolytic expression vector prior to the introducing step. In certain embodiments, the tumor cells include a glioblastoma cell. In some embodiments, the tumor cells include a cancer stem cell. In various embodiments, the subject is a mammal. In some embodiments, the subject is a human.

In various embodiments, the invention teaches an oncolytic expression vector for use in the treatment of intracranial tumor cells in a subject, said oncolytic expression vector including a nucleic acid that includes a nucleotide sequence encoding GADD34, or a biologically active portion thereof, wherein said nucleotide sequence is operably linked to an expression control sequence. In some embodiments, the oncolytic expression vector is a modified herpes virus. In some embodiments, the modified herpes virus is deficient for a $\gamma_1 34.5$ gene. In certain embodiments, the nucleotide sequence includes SEQ ID NO: 1 or a degenerate variant thereof. In various embodiments, the nucleotide sequence includes SEQ ID NO: 2 or a degenerate variant thereof. In some embodiments, the expression control sequence includes a nestin promoter or a biologically active portion thereof. In some embodiments, the expression control sequence includes SEQ ID NO: 3. In certain embodiments, the tumor cells include a glioblastoma cell. In certain embodiments, the tumor cells include a cancer stem cell. In various embodiments, the subject is a mammal. In some embodiments, the subject is a human.

BRIEF DESCRIPTION OF THE DRAWINGS

Exemplary embodiments are illustrated in the referenced figures. It is intended that the embodiments and figures disclosed herein are to be considered illustrative rather than restrictive.

FIGS. 13A and 13B demonstrate, in accordance with an embodiment of the invention, evaluation of the synergistic cytotoxic effect of oHSV1 and TMZ To investigate the synergism of oHSV1 with standard chemotherapeutic drug, temozolomide (TMZ), oHSV1 were diluted serially in 96-well plate and mixed with/without EC30 dose of TMZ (66 µM for U87ΔEGFR) before plating cells at numbers of 5,000. After 5 days, released LDH was measured using CytoTox 96 cytotoxicity assay kit. Synergism was calculated using formula of Chou-Talalay's combination indices (CalcuSyn, BioSoft Inc.). CI: combination index.

DESCRIPTION OF THE INVENTION

Figure 1A:
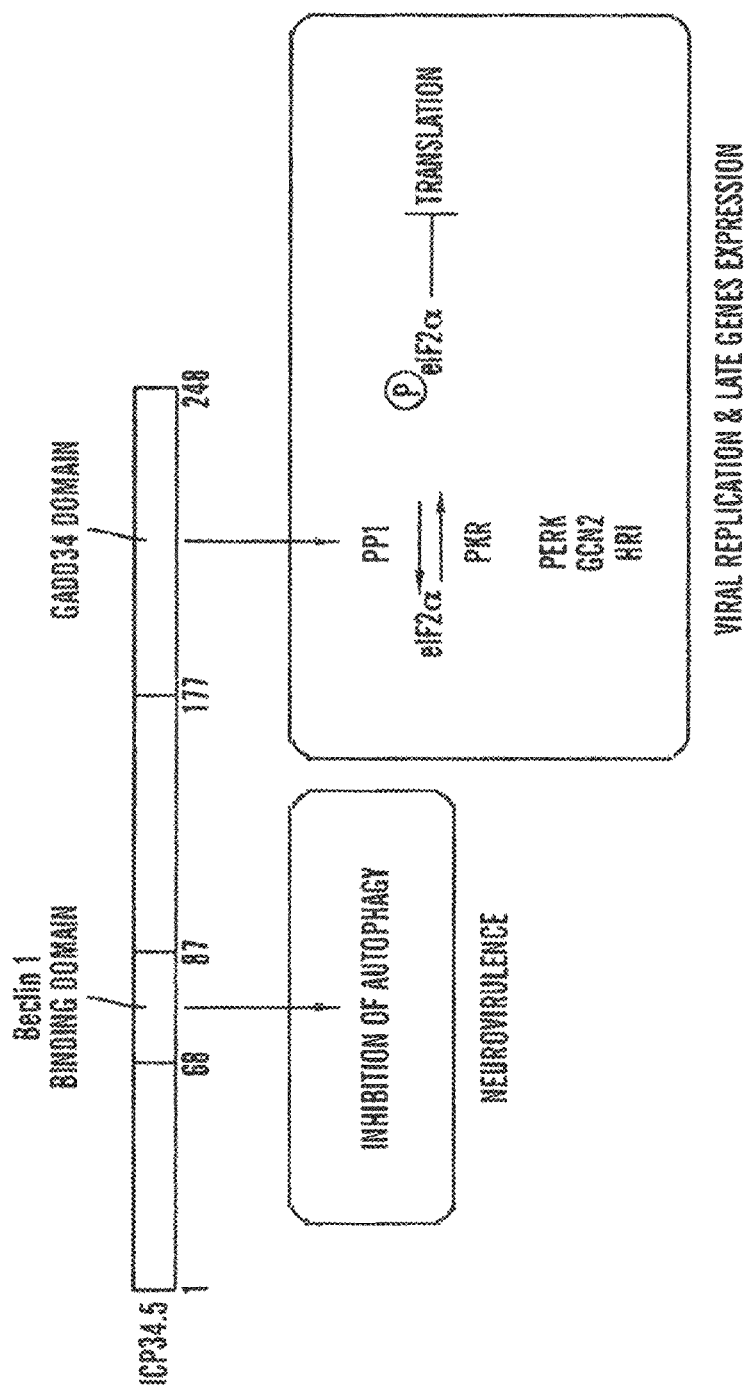
FIG. 1A demonstrates, in accordance with an embodiment of the invention, a schematic representation of ICP34.5. The multifaceted HSV-1 ICP34.5 protein, encoded by the $\gamma_1 34.5$ gene, is typically considered to be 248 a.a., although the lengths are varied by strains. The c-terminal GADD34 homology domain contains PP1a (a.a. 193 to 195) and eIF2α binding domains (a.a. 233-248) to mediate dephosphorylation of phosphorylated eIF2α, the phosphorylated state of which suppresses translation via the PKR-mediated innate immune response pathway in response to HSV1 infection, resulting in significantly reducing viral productivity. The Beclin1 binding domain (a.a. 68-87) exerts an inhibitory effect against autophagy via interaction with Beclin-1, which is an essential protein for the autophagy process. This ICP34.5-mediated antagonism of beclin1 autophagy function is important for viral neurovirulence.
Figures 1B, 1C:
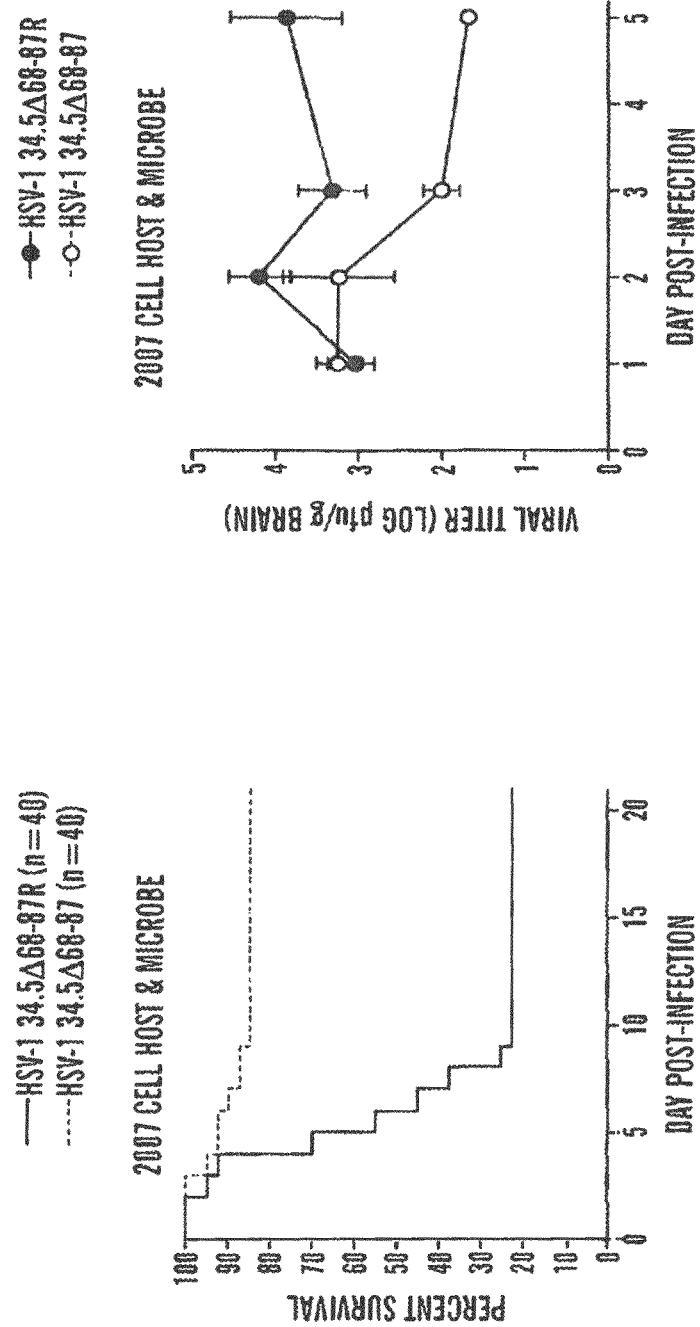
FIGS. 1B and 1C demonstrate, in accordance with an embodiment of the invention, an HSV-1 recombinant virus containing a mutation in ICP34.5 that abrogates binding to Beclin 1 is neuroattenuated in vivo. (B) Survival of C57BL/6J mice infected intracerebrally with 5×10$^5$ pfu of either HSV-1 34.5Δ68-87 or its marker rescue (HSV-1 34.5Δ68-87R). Results shown represent survival data combined from four independent infections. Similar results were observed in each experiment. (C) Viral replication of HSV-1 34.5Δ68-87 and HSV-1 34.5Δ68-87R in brain tissue of infected mice at indicated time after infection. Lower limit of detection=1.7. Data shown represent mean±SEM geometric titer for seven to ten mice per experimental group per time point.
Figure 1E:
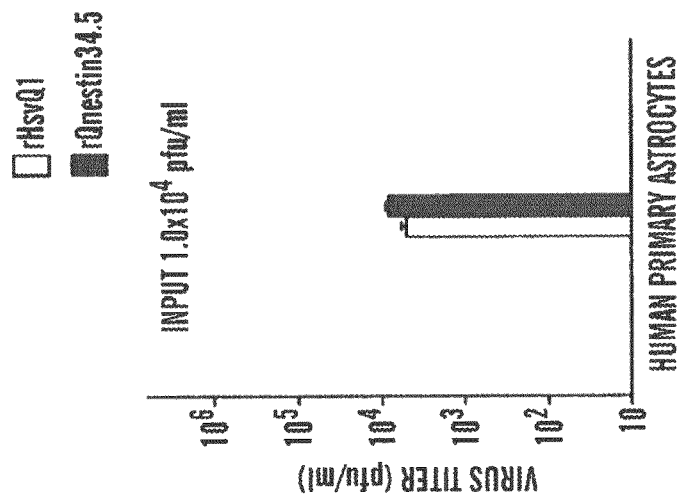
FIGS. 1D and 1E demonstrate, in accordance with an embodiment of the invention, a comparison of the ICP34.5 effect in glioma therapy using oHSV1s. (D) U251, U87dEGFR, U138, MGH238, T98G, and Gli36d5 glioma cells were infected with 10$^4$ pfu of either rHsvQ1 ($\gamma_1 34.5$ gene deletion) or rQNestin34.5 ($\gamma_1 34.5$ gene under the control of a nestin transcriptional promoter). Titers of each sample were determined 3 days after infection. Titers of rQNestin34.5 were higher than those of rHsvQ1 in all glioma cell lines (*, P<0.05, Student's t test.) (E), human astrocytes were infected with either rQNestin34.5 or rHsvQ1 and titers were determined 3 days later. There was no statistically significant difference in values (P>0.1).
Figure 1D:
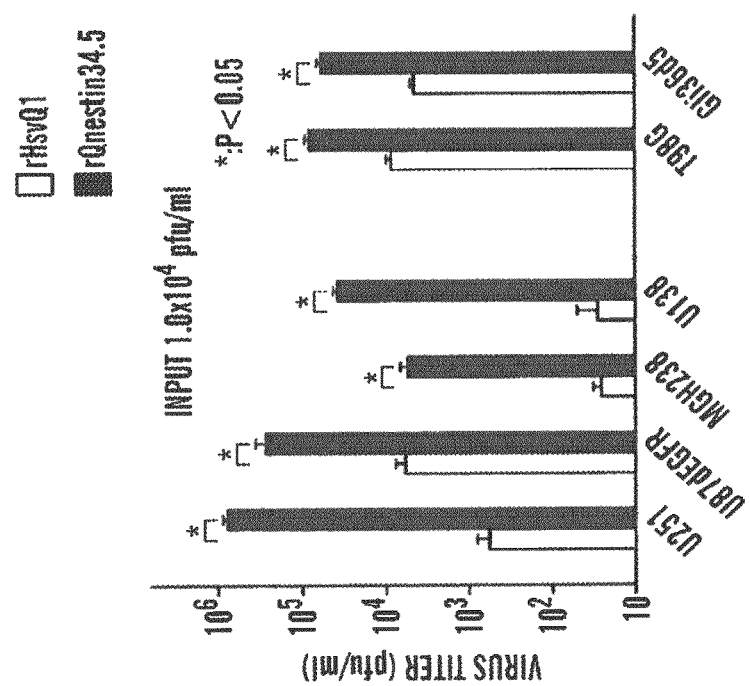
Figure 2:
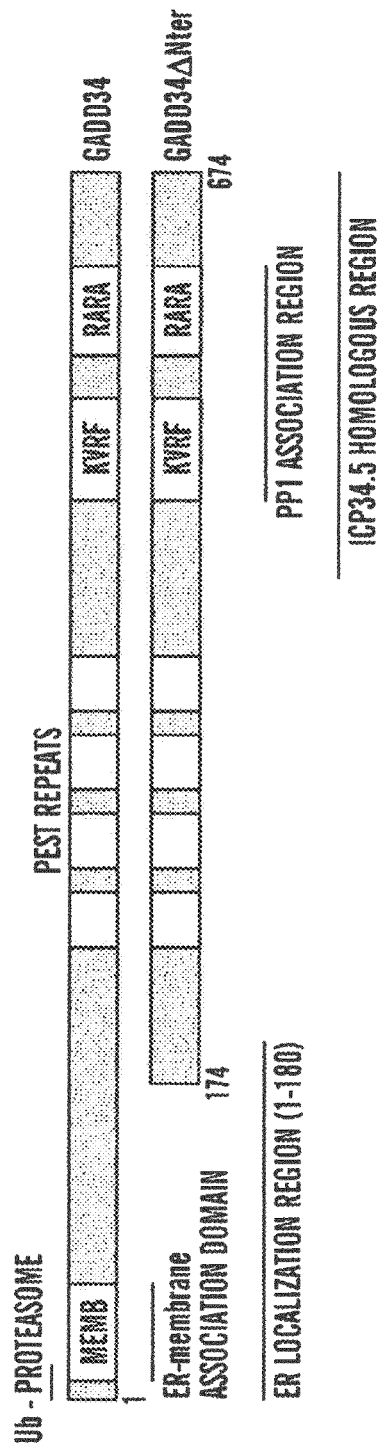
FIG. 2 demonstrates, in accordance with an embodiment of the invention, a schematic representation of GADD34. The human GADD34 gene is mapped on chromosome 19q13.2, a region containing a cluster of DNA repair genes, and has 3 exons and spans at least 2.6 kb (see Hollander et al. Mammalian GADD34, an apoptosis- and DNA damage-inducible gene. J Biol Chem. 1997 May 23; 272(21): 13731-7). GADD34ΔNter lacks the first 174 amino acid (a.a.) or 522 bp of DNA sequence, where the ER-localization domain and Ubiquitin (Ub) proteasome degradation targeting region exist. GADD34 protein has several domains, MEMB at the N-terminal region, PEST repeat in the middle, and KVRF (SEQ ID NO: 7) and RARA (SEQ ID NO: 8) sequences containing ICP34.5 homologous domain at the C-terminal region. MEMB domain contributes to ER-membrane association and the lack of this region or mutations in this helical domain impair localization to the ER and also mitochondria. The regions rich in proline, glutamic acid, serine and threonine (PEST) are generally known to serve as proteolytic signals, but deletion of internal PEST repeats had no impact on GADD34 stability, however it modulated the binding and activity of PP1 to dephosphorylate eIF2α. A bipartite carboxyl terminal domain encompasses the highly conserved KVRF sequence (SEQ ID NO: 7) (a.a. 555-558), a canonical PP1-binding motif, and RARA sequence (SEQ ID NO: 8), which is also required for PP1 binding. GADD34 and SNF5/INI1, which is also known as a tumor suppressor protein and a component of the hSWI/SNF chromatin remodeling complex, can coexist in a trimeric complex with chimeric leukemic HRX fusion proteins, leading to inhibition of GADD34-mediated apoptosis in acute leukemia. And this KVRF (SEQ ID NO: 7) containing region is the site that interacts with SNF5 protein, which also independently binds to the PP1 catalytic subunit, forming a stable trimeric complex of SNF5-PP1-GADD34. Therefore, GADD34 mediates growth suppression and functions as a tumor suppressor, at least in part, through its interaction with SNF5, which may also function as a regulatory subunit of PPI. The N-terminal peptides (1-60 a.a.) exhibit degradation signal peptides with a half-life of <2 h via 26S proteasome.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russell, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

"Mammal," as used herein, refers to a member of the class Mammalia, including, without limitation, humans, as well as nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, newborn subjects and infant subjects, as well as fetuses, whether male or female, are intended to be included within the scope of this term.

The term "vector," as used herein, refers to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both of which are incorporated herein by reference). Additionally, the techniques described herein and demonstrated in the referenced figures are also instructive with regard to effective vector construction.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "promoter," as used herein, refers to a nucleic acid sequence that regulates, either directly or indirectly, the transcription of a corresponding nucleic acid coding sequence to which it is operably linked. The promoter may function alone to regulate transcription, or, in some cases, may act in concert with one or more other regulatory sequences such as an enhancer or silencer to regulate transcription of the gene of interest. The promoter comprises a DNA regulatory sequence, wherein the regulatory sequence is derived from a gene, which is capable of binding RNA polymerase and initiating transcription of a downstream (3'-direction) coding sequence. A promoter generally comprises a sequence that functions to position the start site for RNA synthesis. The best-known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one can position the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter used, individual elements can function either cooperatively or independently to activate transcription. The promoters described herein may or may not be used in conjunction with an "enhancer," which refers to a cis-acting regulatory sequence involved in the transcriptional activation of a nucleic acid sequence, such as those for the genes, or portions or functional equivalents thereof, listed herein.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages may be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta-lactamase (penicillinase), lactose and tryptophan (trp) promoter systems. As demonstrated herein, in some embodiments, a nestin promoter is used to drive expression of the gene of interest. In addition to producing nucleic acid sequences of promoters and enhancers synthetically, sequences may be produced using recombinant cloning and/or nucleic acid amplification technology, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

The term "recombinant HSV-1 vector," as used herein, defines a recombinant HSV-1 vector comprising: (a) the DNA of, or corresponding to, at least a portion of the genome of an HSV-1 that is capable of transducing into a target cell at least one selected gene and is capable of promoting replication and packaging; and (b) at least one selected gene (or transgene) operatively linked to at least one regulatory sequence directing its expression, the gene flanked by the DNA of (a) and capable of expression in the target cell in vivo or in vitro. Thus, a "recombinant HSV" (rHSV) means HSV that has been genetically altered, e.g., by the addition or insertion of a selected gene.

A "gene," or a "sequence which encodes" a particular protein, is a nucleic acid molecule which is transcribed (in the case of DNA) and translated (in the case of mRNA) into a polypeptide in vitro or in vivo when placed under the control of one or more appropriate regulatory sequences. A gene of interest can include, but is no way limited to, cDNA from eukaryotic mRNA, genomic DNA sequences from eukaryotic DNA, and even synthetic DNA sequences. A transcription termination sequence will usually be located 3' to the gene sequence. Typically, a polyadenylation signal is provided to terminate transcription of genes inserted into a recombinant virus.

The term "polypeptide" or "protein," as used herein, means a polymer of amino acids joined in a specific sequence by peptide bonds. As used herein, the term "amino acid" refers to either the D or L stereoisomer form of the amino acid, unless otherwise specifically designated.

The term "transgene" refers to a particular nucleic acid sequence encoding a polypeptide or a portion of a polypeptide to be expressed in a cell into which the nucleic acid sequence is inserted. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been inserted; (3) a nucleic acid sequence that serves to add additional copies of the same (i.e., homologous) or a similar nucleic acid sequence naturally occurring in the cell into which it has been inserted, or (4) a silent naturally occurring or homologous nucleic acid sequence whose expression is induced in the cell into which it has been inserted. A "mutant form" or "modified nucleic acid" or "modified nucleotide" sequence means a sequence that contains one or more nucleotides that are different from the wild-type or naturally occurring sequence, i.e., the mutant nucleic acid sequence contains one or more nucleotide substitutions, deletions, and/or insertions. In some cases, the gene of interest may also include a sequence encoding a leader peptide or signal sequence such that the transgene product may be secreted from the cell.

As used herein, the term "transfection" refers to the uptake of foreign DNA by a mammalian cell. A cell has been "transfected" when exogenous DNA has been introduced inside the cell membrane. A number of transfection techniques are known in the art. See, Graham et al. (1973) Virology, 52:456; and Sambrook et al. (1989) Molecular Cloning, a laboratory manual, Cold Spring Harbor Laboratories, New York. Such techniques can be used to introduce one or more exogenous DNA moieties, such as a viral vector and other nucleic acid molecules, into suitable host cells. The term refers to both stable and transient uptake of the genetic material.

The term "oncolytic activity," as used herein, refers to cytotoxic effects in vitro and/or in vivo exerted on tumor cells without any appreciable or significant deleterious effects to normal cells under the same conditions. The cytotoxic effects under in vitro conditions are detected by various means as known in prior art, for example, by staining with a selective stain for dead cells, by inhibition of DNA synthesis, or by apoptosis. Detection of the cytotoxic effects under in vivo conditions is performed by methods known in the art.

A "biologically active" portion of a molecule, as used herein, refers to a portion of a larger molecule that can perform a similar function as the larger molecule. Merely by way of non-limiting example, a biologically active portion of a promoter is any portion of a promoter that retains the ability to influence gene expression, even if only slightly. Similarly, a biologically active portion of a protein is any portion of a protein which retains the ability to perform one or more biological functions of the full-length protein (e.g. binding with another molecule, phosphorylation, etc.), even if only slightly.

With the aforementioned preliminary descriptions and definitions in mind, additional background is provided herein below to provide context for the genesis and development of the inventive vectors, compositions and methods described herein.

Current mutant HSV-1 vectors that target malignant glioma are based on the two deletion mutant genes, ICP6 ($U_L39$ gene product), the large subunit of HSV-1 ribonucleotide reductase (RR), and ICP34.5 (34.5 gene product), a multifunctional protein that is also related to neurovirulence. While the lack of ICP6 restricts virus replication to non-dividing cells but allows replication to continue in cells with defects in the p16 tumor suppressor pathway, deletions of both 72 34.5 genes suppresses HSV-1 encephalitis. While not wishing to be bound by any one particular theory, this may be due to ICP34.5's facilitation of Beclin-1 autophagy function, essential for neurovirulence. Besides this autophagic inhibitory effect, ICP34.5 also counteracts a host defense mechanism triggered by viral infection. This mechanism activates PKR (double-stranded RNA protein kinase) that then phosphorylates the translation factor, eIF2α, leading to translation inhibition. ICP34.5 directly binds and activates PP1 (protein phosphatase 1) that dephosphorylates eIF2α, allowing for viral mRNA translation to continue. Oncolytic HSV-1 with mutated γ34.5 genes (e.g. G207, 1716) has proven to be safe for administration in humans with gliomas in multiple clinical trials, but efficacy has been elusive, probably due to their limited viral replication.

To overcome this limitation, an HSV1 was previously engineered, wherein the ICP34.5 gene is under the transcriptional control of the glioma stem cell promoter for nestin. rQNestin34.5 has exhibited increased efficacy in glioma models and currently a phase I clinical trial in adults with glioblastoma is being pursued. However, there remains a potential concern with expression of ICP34.5 in the brain, particularly in individuals (children and young adults) whose brains may still be relatively rich with nestin-positive neural progenitor cells and where expression of ICP34.5 could trigger neurovirulence. Expression of ICP34.5 has also been reported to contribute to Alzheimer disease and other neurodegenerative diseases by suppressing autophagy function in neurons. Finally, ICP34.5's autophagy inhibition may reduce the therapeutic efficacy of conventional chemo- and radiotherapies that rely on autophagy-mediated tumor cell death in apoptosis-resistant malignant gliomas.

Growth Arrest and DNA-Damage inducible gene 34 (GADD34), also known as PPP1R15A, was discovered by screening a radiation-treated myeloblastic leukemia cell cDNA library. Treatment of various human cell lines with DNA-damaging agents enhanced expression of GADD34. A stress-inducible GADD34 protein also interacts with PP1 and reverses phosphorylation of eIF2α, preventing complete shutoff of protein synthesis during stress conditions in the same way as ICP34.5 does, since its c-terminus shares significant homology with the C-terminus of GADD34. Apart from enhanced protein synthesis via the PP1 complex during conditions of cellular stress, GADD34 forms a stable complex with tuberous sclerosis complex (TSC) ½, causes TSC dephosphorylation, and inhibits the mTOR signaling pathway. Therefore, GADD34 could be a potential mTOR inhibitor for cancer therapy. In fact, conditionally ectopic GADD34 overexpression in U251 human glioma cells likely induced cell growth delay and senescence (data not shown). This mTOR suppression via TSC1-GADD34 complex can also induce cytoprotective autophagy under the condition of misfolded mutant protein expression and during starvation. In addition, recently GADD34 was reported as a neuroprotective factor in neurodegenerative disease, including Alzheimer's, Parkinson's and prion diseases. Neurodegenerative diseases are associated with the accumulation of misfolded disease-specific proteins, triggering the unfolded protein response (UPR) pathway, resulting in the transient shutdown of protein translation, through phosphorylation of eIF2 alpha. In prion-diseased mice, overexpression of GADD34 restored vital translation rates during prion disease, rescuing synaptic deficits and neuronal loss, thereby significantly increasing survival.

Because it is a stress inducible factor, turnover of GADD34 protein is rapid and the N-terminal peptides (1-60 a.a.) exhibit a degradation signal peptide (degron) with a half-life of <2 h via 26S proteasome. Of note, it was recently reported that phosphorylation of tyrosine-262 also contributes to the rate of GADD34 turnover and a non-phosphorylation mutant form (Y262F) displayed a significant increase $t_{1/2}$>2 hr. Also, the N terminal 180 residues of GADD34 directs the localization to the endoplasmic reticulum (ER) and it targets the alpha isoform of PP1 to the ER. Interestingly, while this N-terminal truncated form (180-674aa) still retains the capacity to dephosphorylate eIF2 alpha via PP1, it lacks ER specific localization. A truncated mutant (513-674aa), which encompassed the ICP34.5 homology domain, was exclusively in nucleoli and lacks the capability of dephosphorylation of eIF2 alpha.

Overall, these findings indicate that the use of GADD34 in an oncolytic HSV1 vector can enhance therapeutic efficacy, while reducing cytotoxicity in non-cancer cells. Because of the dual roles of GADD34 of enhanced protein synthesis via dephosphorylation of eIF2α, and induction of autophagy via TSC1/mTOR pathway, it could support viral replication in cancer cells and circumvent the limitation of ICP34.5 expression leading to possible neurovirulence in response to oHSV1 infection.

An N terminal truncated form (GADD34ΔN) was evaluated, in which the first 174 amino acids residues were deleted to prevent rapid degradation of GADD34 protein and to suppress potential ER-stress induction. To prove the hypothesis that GADD34 expression in the context of oHSV allows for robust replication and cytotoxicity in glioma cells, but not in normal cells, novel HSV1 oncolytic viruses, NG34 and NG34C, were designed to express the full length (1-674aa) and the N-terminal truncated form (175-674aa) of the GADD34 gene under the control of a nestin promoter, respectively. A summary of the relevant characteristics discovered, and described above, is provided in Table I.

TABLE I

Summary

|  | HSV1 ICP34.5 | wt GADD34 (1-674aa) | GADD34ΔNter (175-674aa) |
|---|---|---|---|
| PP1 interaction | + | + | + |
| eIF2α dephosphorylation | + | + | + |
| ER localization | − | + | − |
| Beclin-1 interaction | + | − | − |
| TSC dephosphorylation | − | + | + |
| Proteasomal degradation | − | + | − |
| Autophagy activity | Down | Up | Up |
| neurovilurence | + | No report | No report |
| Neuroprotective effect | Down | Up | Up |

With the foregoing findings in mind, certain embodiments of the invention teach an oncolytic expression vector. In some embodiments, the oncolytic expression vector includes a nucleic acid including a nucleotide sequence of interest which encodes the GADD34 protein, a biologically active portion thereof (such as a truncated version thereof), or a functional equivalent thereof. In certain embodiments, the nucleotide sequence of interest is operably linked to an expression control sequence. In some embodiments, the expression control sequence included in the oncolytic expression vector is a promoter. In some embodiments, the promoter is a nestin promoter. In certain embodiments, the oncolytic vector is a recombinant HSV-1 vector. In some embodiments, the recombinant HSV-1 vector is deficient for the 7134.5 gene. In various embodiments, the nucleotide sequence encoding the GADD34 protein includes SEQ ID NO: 1 or a degenerate variant of SEQ ID NO: 1. In some embodiments, the nucleotide sequence encodes a truncated GADD34 gene. In some embodiments, the truncated GADD34 gene is GADD34C. GADD34C is encoded by SEQ ID NO: 2. One of skill in the art would readily appreciate that a degenerate variant of SEQ ID NO: 2 could be used as an alternative to SEQ ID NO: 2. In some embodiments, the expression control sequence includes the nestin promoter, as demonstrated in SEQ ID NO: 3. One of skill in the art would readily appreciate that a modified version of SEQ ID NO: 3 could also be used, so long as it retains similar biological activity. Merely by way of non-limiting example, the nestin $2^{nd}$ intron sequence (enhancer) represented in SEQ ID NO: 4, and the hsp68 minimum promoter represented in SEQ ID NO: 5, could be used alone or combined when designing various constructs contemplated herein. In some embodiments, the nestin enhancer element may be operably linked to a heat shock protein 68 (hsp68) minimum promoter to drive the expression of GADD34 delta-Nter, as demonstrated in SEQ ID NO: 6. In some embodiments, alternative or additional expression control sequences may be incorporated into the oncolytic expression vectors to initiate or influence the expression of any of the aforementioned nucleotide sequences of interest. Merely by way of non-limiting examples, any tumor- or tissue-specific promoter or other expression control sequences, such as microRNA target sequences, may be used. Examples of specific promoters included, but are not limited to, CEA for colon cancer cells, Muc1 for breast cancer cells, Myb1 for all cancer cells, Tyrosinase for melanoma cells, PSA for prostate cancer cells. Examples of miR translational control sequences include, but are not limited to: miR128 or miR124 to differentiate glioma cells from normal neural cells. In some embodiments, alternative oncolytic expression vectors, aside from HSV-1, can be used to facilitate the expression of GADD34, GADD34C, or one or more biologically active portions thereof.

In various embodiments, the present invention provides a method for treating a neoplastic disease in a subject. In certain embodiments, the method includes administering to the subject a therapeutically effective amount of an expression vector with oncolytic activity. In some embodiments, the expression vector is a tumor-specific conditional replication vector. In some embodiments, the vector is a recombinant HSV-1 vector. In some embodiments, the recombinant HSV-1 vector includes one or more copies of a DNA sequence of interest encoding a GADD34 protein, one or more portions of the GADD34 protein, or a functional equivalent of the GADD34 protein. In some embodiments, the DNA sequence of interest is GADD34C. In some embodiments, one or more of the aforementioned DNA sequences is operably linked to an expression control sequence, which may include any of those expression control sequences described herein above. In some embodiments, the expression control sequence is a promoter configured to facilitate expression of the DNA sequence. In some embodiments the promoter is a nestin promoter. In some embodiments, an alternative promoter, such as any of those described herein, or designed according to the methods described herein, can be used. In some embodiments, the neoplastic disease that is treated is cancer. In some embodiments, the cancer is brain cancer. Merely by way of non-limiting examples, the types of brain cancer that can be treated may include glioblastoma, anaplastic astrocytoma, astrocytoma, pilocytic astrocytoma, diffuse intrinsic pontine glioma, oligodendroglioma, anaplastic oligodendroglioma, mixed oligo-astrocytoma, and pendymoma. In some embodiments, cancer stem cells are treated with the inventive method. In some embodiments, the subject treated is a mammal. In certain embodiments, the subject treated is a human.

Methods of treating any of the neoplastic diseases described herein, including brain cancer, may include administration of the compounds of exemplary embodiments as a single active agent, or in combination with additional methods of treatment including, but not limited to, stem cell-based therapy, immunotherapy, radiation therapy, therapy with immunosuppressive agents, chemotherapeutic or anti-proliferative agents, including cytokines. The methods of treatment of the invention may be in parallel to, prior to, or following additional methods of treatment.

As indicated above, the GADD34 or GADD34C DNA sequences, or portions thereof that can be used in conjunction with the inventive constructs and methods described herein include those that have been modified. When expressed, modified DNA sequences include those that can result in amino acid substitutions (e.g., at one or more of the important amino acid residues) of the GADD34 or GADD34C protein. A modified GADD34 or GADD34C protein can have altered biological activity (increased or decreased) or substantially the same activity (functionally equivalent), as compared to unmodified GADD34 or GADD34C protein, especially with regard to facilitating dephosphorylation of eIF2 alpha.

The promoter operably linked to the gene of interest, which can include but is not limited to the GADD34 gene, N-terminal truncated GADD34 gene, otherwise modified GADD34 gene, or functional equivalent of the GADD34 gene, used in the vectors, compositions and methods described herein, is preferably a promoter that can drive expression of the gene of interest in a cancer cell. In preferred embodiments, the promoter used in the inventive vectors, compositions and methods facilitates levels of expression of the gene of interest that are sufficient to result in (1) reduced phosphorylation of eIF2 alpha, and/or (2) significant viral replication, and/or (3) significant oncolysis, such that some therapeutic benefit results. "Therapeutic benefit," as used herein, includes any decrease in cancer cell number, cancer cell proliferation rate, or metastasis. In some embodiments, the promoter used herein facilitates selective or increased expression of the associated gene of interest in one or more cancer cell type of interest, compared to a normal cell.

The term "operably linked," as used herein, refers to the arrangement of various nucleic acid molecule elements relative to each other such that the elements are functionally connected and are able to interact with each other. Such elements may include, without limitation, a promoter, an enhancer, a polyadenylation sequence, one or more introns and/or exons, and a coding sequence of a gene of interest to be expressed. The nucleic acid sequence elements, when operably linked, can act together to modulate the activity of one another, and ultimately may affect the level of expression of the gene of interest, including any of those encoded by the sequences described above.

The nucleic acid sequence of the "full length" GADD34 gene used in the experiments reported herein and described in the referenced figures is provided herein as SEQ ID NO: 1. The nucleic acid sequence of the N-terminal truncated GADD34 gene is provided herein as SEQ ID NO: 2. The nucleic acid sequence of the nestin promoter control sequence used in the experiments reported herein is provided as SEQ ID NO: 3. Although these specific sequences are provided, the nucleic acid molecules used in the inventive vectors, compositions and methods are not limited strictly to molecules including the sequences set forth as SEQ ID NO: 1, SEQ ID NO: 2, SEQ ID NO: 3, SEQ ID NO: 4, SEQ ID NO: 5 and SEQ ID NO: 6. Rather, specific embodiments encompass nucleic acid molecules carrying modifications such as substitutions, small deletions, insertions, or inversions. Included in the invention are nucleic acid molecules, the nucleotide sequence of which is at least 95% identical (e.g., at least 96%, 97%, 98%, or 99% identical) to the nucleotide sequence shown as SEQ ID NOS: 1, 2, 3, 4, 5, and 6 in the Sequence Listing.

Also included in the invention is a nucleic acid molecule that has a nucleotide sequence which is a degenerate variant of a nucleic acid disclosed herein, e.g., SEQ ID NOS: 1, 2, 3, 4, 5, and 6. A sequential grouping of three nucleotides, a "codon," encodes one amino acid. Since there are 64 possible codons, but only 20 natural amino acids, most amino acids are encoded by more than one codon. This natural "degeneracy" or "redundancy" of the genetic code is well known in the art. It will thus be appreciated that the nucleic acid sequences shown in the Sequence Listing provide only an example within a large but definite group of nucleic acid sequences that will encode the polypeptides as described above.

Importantly, the vectors of the embodiments described herein may be useful for the introduction of additional genes in gene therapy. Thus, for example, the HSV vectors of this invention may contain one or more additional exogenous gene for the expression of a protein effective in regulating the cell cycle, such as p53, Rb, or mitosin, or a biologically active variant thereof, or in inducing cell death, such as the conditional suicide gene thymidine kinase, the latter must be used in conjunction with a thymidine kinase metabolite in order to be effective, or any other anti-tumor gene, such as for example a toxin.

When used pharmaceutically, oncolytic vector embodiments discussed herein can be combined with various pharmaceutically acceptable carriers. Suitable pharmaceutically acceptable carriers are well known to those of skill in the art. The compositions can then be administered therapeutically or prophylactically, in effective amounts, described in greater detail below.

As used herein, the term "therapeutically effective amount" is intended to mean the amount of vector which exerts oncolytic activity, causing attenuation or inhibition of tumor cell proliferation, leading to tumor regression. An effective amount will vary, depending upon the pathology or condition to be treated, by the patient and his or her status, and other factors well known to those of skill in the art. Effective amounts are easily determined by those of skill in the art. In some embodiments a therapeutic range is from $10^3$ to $10^{12}$ plaque forming units introduced once. In some embodiments a therapeutic dose in the aforementioned therapeutic range is administered at an interval from every day to every month via the intratumoral, intrathecal, convection-enhanced, intravenous or intra-arterial route.

Although certain routes of administration are provided in the foregoing description, according to the invention, any suitable route of administration of the vectors may be adapted, and therefore the routes of administration described above are not intended to be limiting. Routes of administration may including but are not limited to, intravenous, oral, buccal, intranasal, inhalation, topical application to a mucosal membrane or injection, including intratumoral, intradermal, intrathecal, intracisternal, intralesional or any other type of injection. Administration can be effected continuously or intermittently and will vary with the subject and the condition to be treated. One of skill in the art would readily appreciate that the various routes of administration described herein would allow for the inventive vectors or compositions to be delivered on, in, or near the tumor or targeted cancer cells. One of skill in the art would also readily appreciate that various routes of administration described herein will allow for the vectors and compositions described herein to be delivered to a region in the vicinity of the tumor or individual cells to be treated. "In the vicinity"

can include any tissue or bodily fluid in the subject that is in sufficiently close proximity to the tumor or individual cancer cells such that at least a portion of the vectors or compositions administered to the subject reach their intended targets and exert their therapeutic effects.

Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer the compositions of the invention to a cell in vitro or to a subject in vivo. A pharmaceutically acceptable carrier can contain a physiologically acceptable compound that acts, for example, to stabilize the composition or to increase the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide. For example, a physiologically acceptable compound such as aluminum monosterate or gelatin is particularly useful as a delaying agent, which prolongs the rate of absorption of a pharmaceutical composition administered to a subject. Further examples of carriers, stabilizers or adjutants can be found in Martin, Remington's Pharm. Sci., 15th Ed. (Mack Publ. Co., Easton, 1975), incorporated herein by reference.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Vector Constructs of the NG34 and NG34C Oncolytic Viruses

Figure 3:
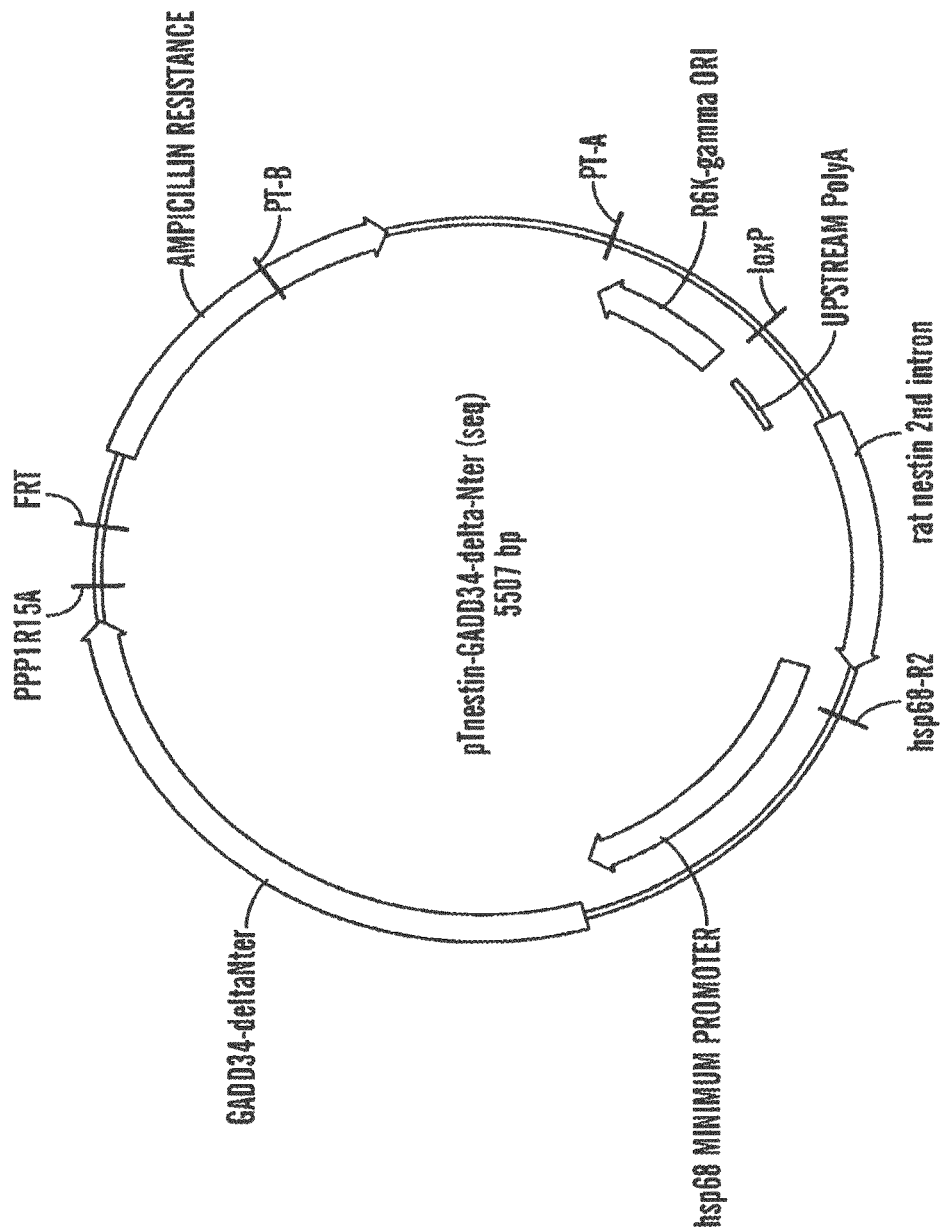
FIG. 3 demonstrates, in accordance with an embodiment of the invention, a schematic map of pTnestin-GADD34ΔNter. Full-length or N-terminal truncated GADD34 gene was inserted into NcoI/HpaI sites of pTnestin-luc-b vector that inserts the nestin-hsp68 promoter-enhancer element into pTransfer, by ligating the fragment obtained by enzymatic digestion of blunt-ended BstXI/XhoI or HpaI/XhoI of a pOTB7-GADD34 (SEQ ID NO: 1), respectively. Resulting constructs were called pTnestin-GADD34 or pTnestin-GADD34ΔNter. Those shuttle vectors were used to make fHsvQuik-based oHSV1 as described in FIG. 4.
Figure 4A:
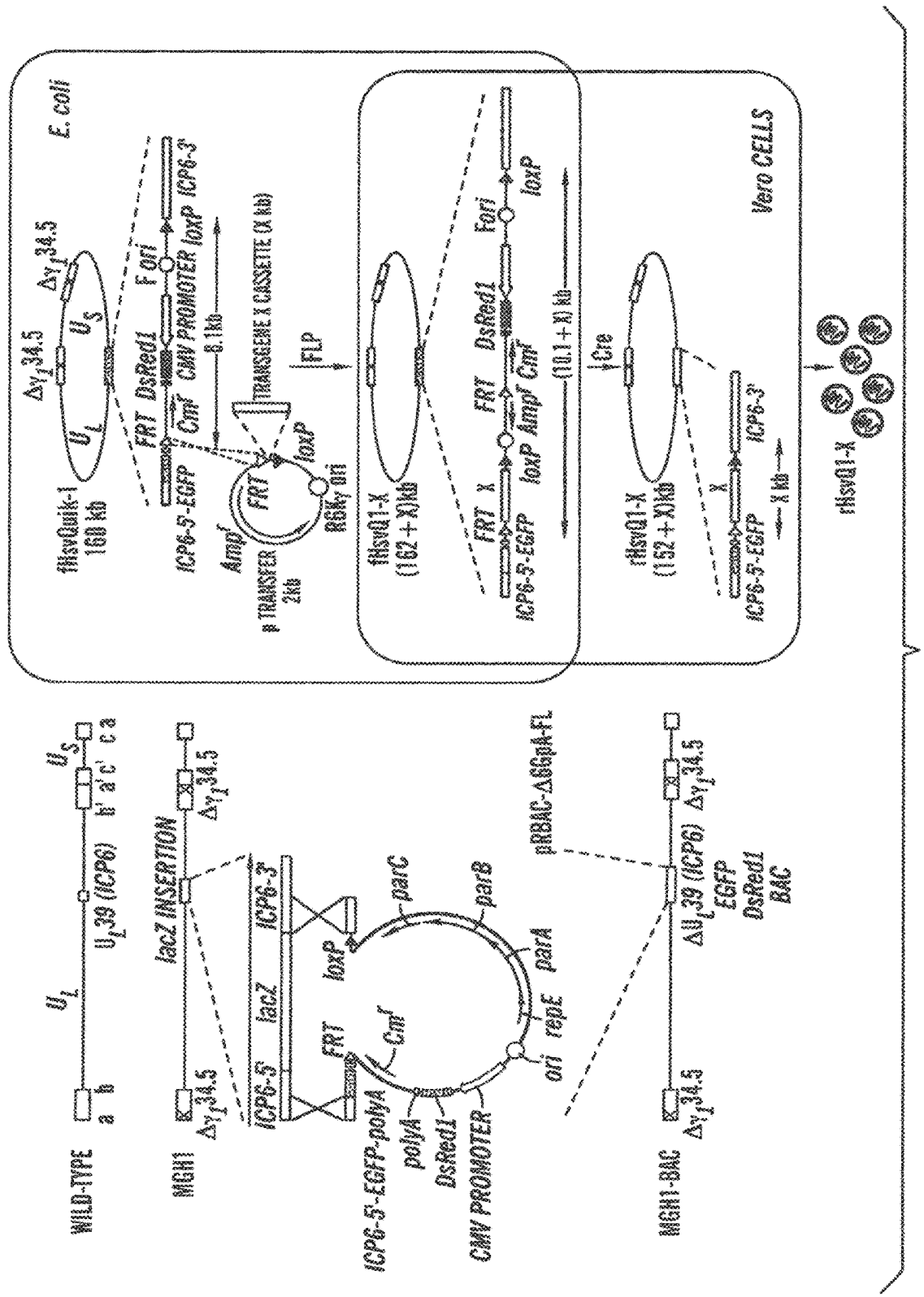
FIG. 4A demonstrates, in accordance with an embodiment of the invention, a schematic strategy of cloning MGH1 genome into a BAC vector. MGH1 is a strain F-derived HSV-1 mutant that possesses deletions in both copies of the g 1 34.5 gene and a lacZ insertion at the UL 39 locus. A UL 39-targeting BAC plasmid, pRBAC-D6GpA-FL, was constructed so that it contains two homology arms that can recombine with the viral genome upstream and downstream of the lacZ insertion within the UL 39 locus. The construct also has (1) a set of two recombination sequences, loxP and FRT sites, flanking the BAC backbone, (2) an EGFP expression cassette which is inserted in-frame downstream of the truncated UL 39 coding sequence and (3) an RFP expression cassette within the BAC backbone. The linearized pRBAC-D6GpA-FL DNA and intact MGH1 virion DNA were co-transfected into Vero cells, and recombinant virus that carries the BAC sequence (MGH1-BAC) was isolated. The transgene cassette of interest (X) is first cloned into a pTransfer shuttle plasmid and the resulting plasmid (pTransfer-X) is electroporated together with an FLP-expressing helper plasmid into bacteria carrying fHsvQuik-1 BAC plasmid. Co-integrants of the pTransfer-X and fHsvQuik-1 fused at the FRT sites (fHsvQ1-X) can be readily obtained by selection with Cm and Amp at 43° C. The fHsvQ1-X has the transgene cassette inserted at the UL 39 locus and two unidirectional loxP sites are now flanking all the procaryotic plasmid backbones as well as the RFP marker gene. Upon co-transfection of the fHsvQ1-X and a Cre-expressing helper plasmid into Vero cells, the procaryotic plasmid backbones, together with the RFP expression cassette, can be excised through Cre-mediated site-specific recombination. As a result, recombinant HSV vectors with the transgene cassette (rHsvQ1-X) can be rescued.
Figure 4B:
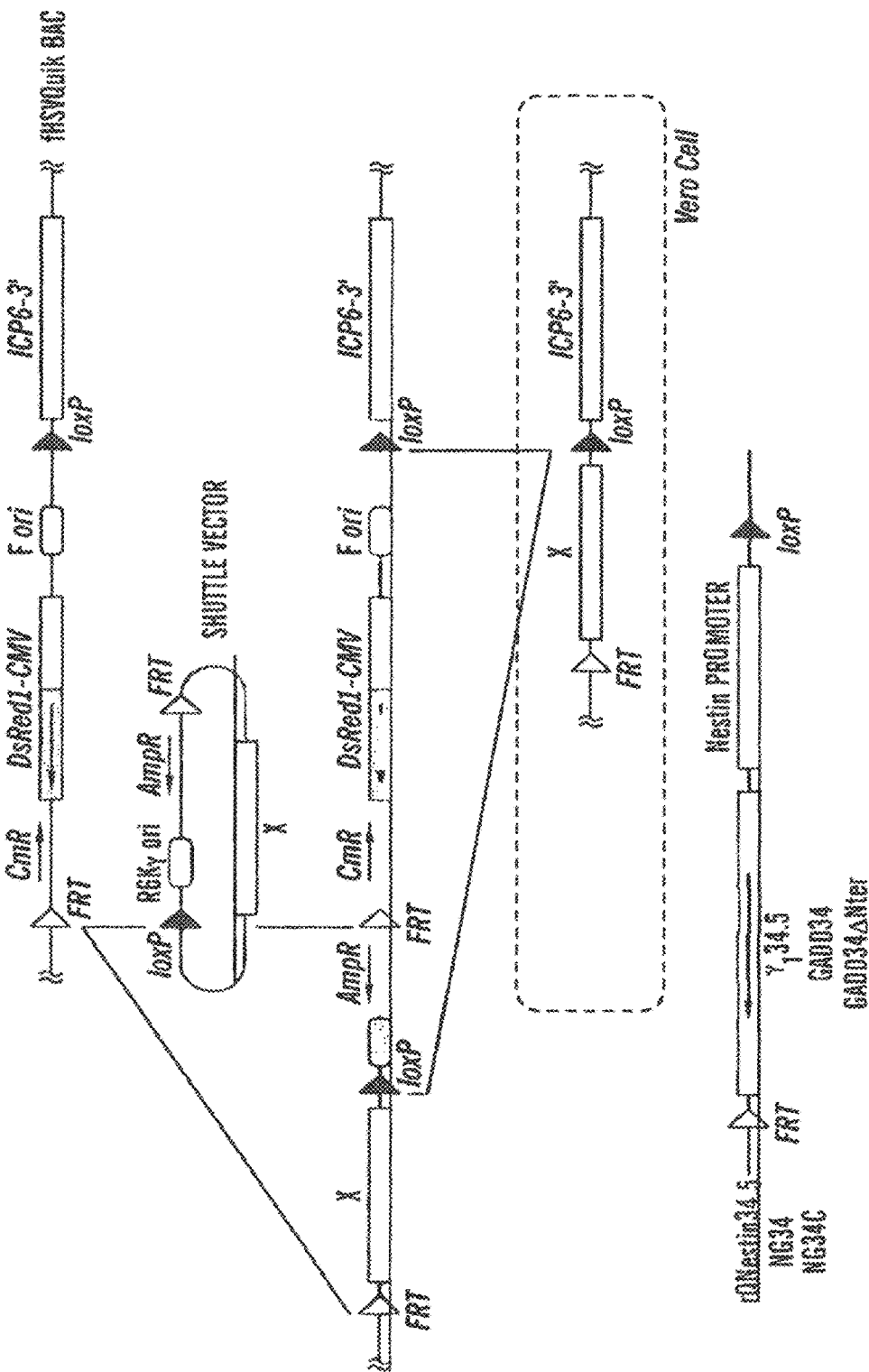
FIG. 4B demonstrates, in accordance with an embodiment of the invention, novel oncolytic HSV1, NG34 and NG34C. Using a BAC-based oncolytic HSV1 vector (ΔICP6 and ΔICP34.5 product genes) system that is called as "HSVQuik system" (see Gene Ther 13(8):705-14, 2006, which is incorporated herein by reference in its entirety), two oHSV1 vectors were developed, which insert full-length and N-terminal truncated human gene derived GADD34 gene under control of nestin promoter that is active in glioma cells, where previously developed rQNesting34.5 harbors one copy of gamma(1)34.5 gene (see Cancer Res. 2005 Apr. 1; 65(7):2832-9, which is incorporated herein by reference in its entirety).
Figure 5A:
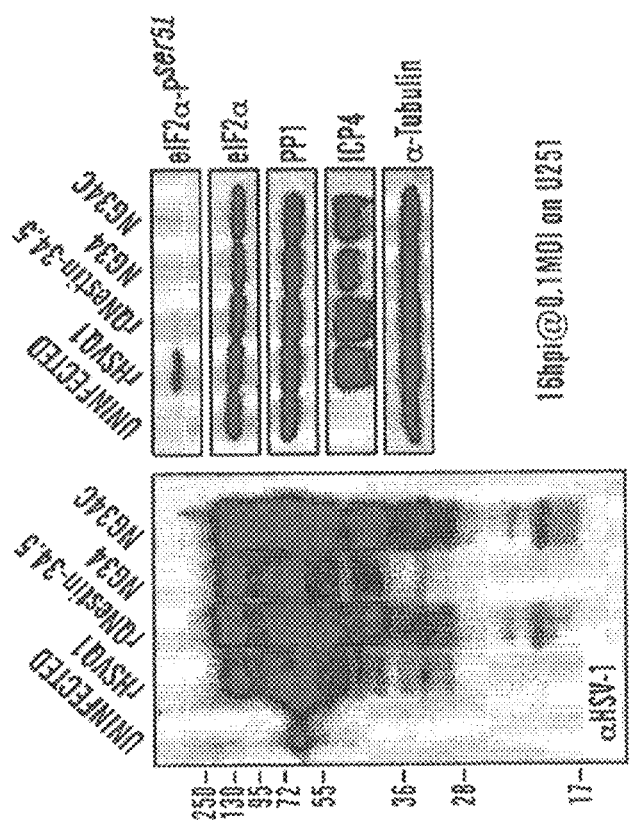
FIG. 5A demonstrates, in accordance with an embodiment of the invention, phosphorylation of eIF2α was suppressed in response to NG34 and NG34C infection in glioma. Western Blotting of cell lysates at 16 h post-infection of oHSV1 at MOI of 0.1 showed that while ICP34.5-null mutant rHSVQ1 (ΔICP6, ΔICP34.5) infection resulted in strong phosphorylation of eIF2α to suppress translational initiation, NG34 and NG34C viruses, as well as rQNestin34.5 reversed the phosphorylation levels. Antibodies against HSV-1, eIF2α, phospho(Ser51)-eIF2α, PP1, ICP4 and αTubulin were used in the assay.
Figure 5B:
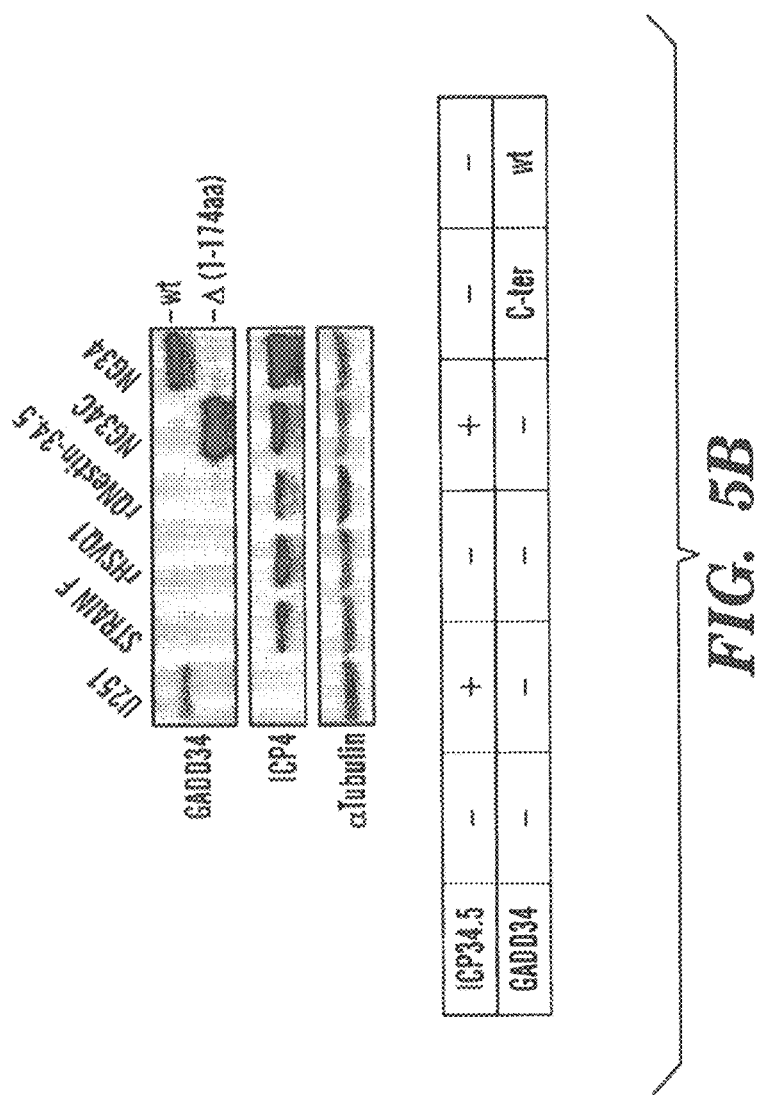
FIG. 5B demonstrates, in accordance with an embodiment of the invention, GADD34 expression upon NG34 and NG34C infection. Full-length GADD34 or N-terminal region truncated GADD34 was overexpressed from cells in response to NG34 and NG34C infection, respectively, at 16 h post-infection at MOI of 0.1, while wild-type HSV1 strain F and other GADD34 noncoding oHSV1 infection did not cause GADD34 expression. Western blots were performed using antibodies against GADD34, ICP4 and αTubulin.
Figure 6A:
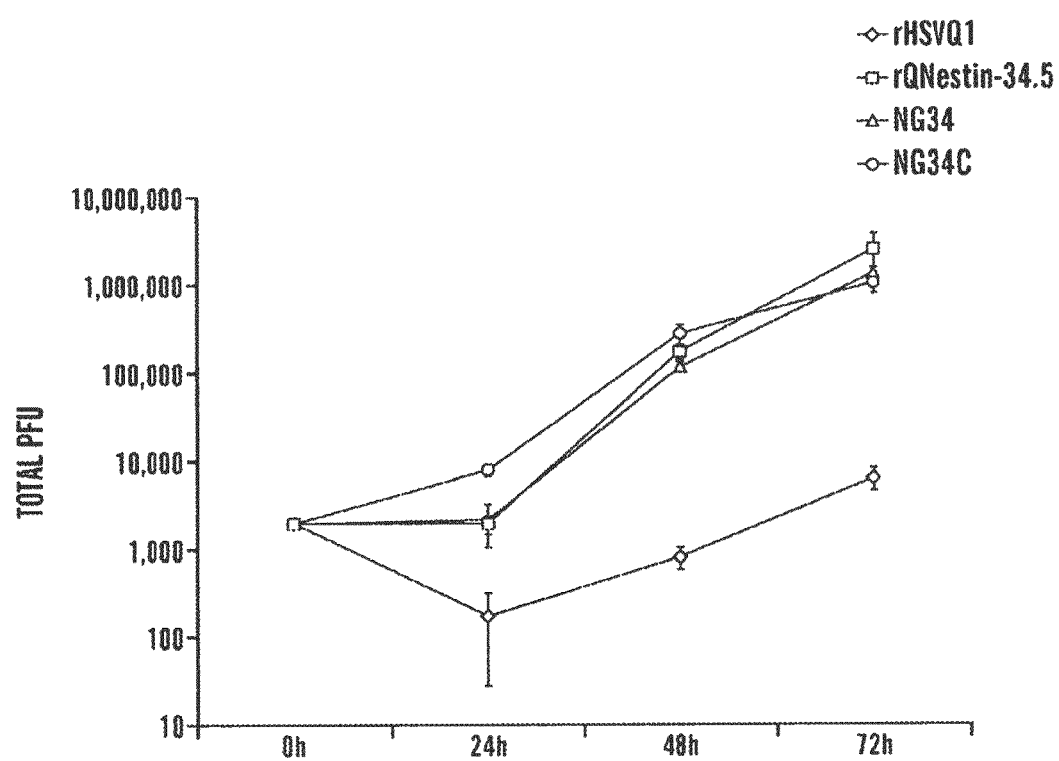
FIG. 6A demonstrates, in accordance with an embodiment of the invention, the rapid viral life cycle of NG34C in glioma cells. Four different oHSV1 were infected into U251 cells for 24, 48 and 72 hours before collecting cells and media. Titrations were performed on Vero cells to measure plaque forming units (PFU).
Figure 6B:
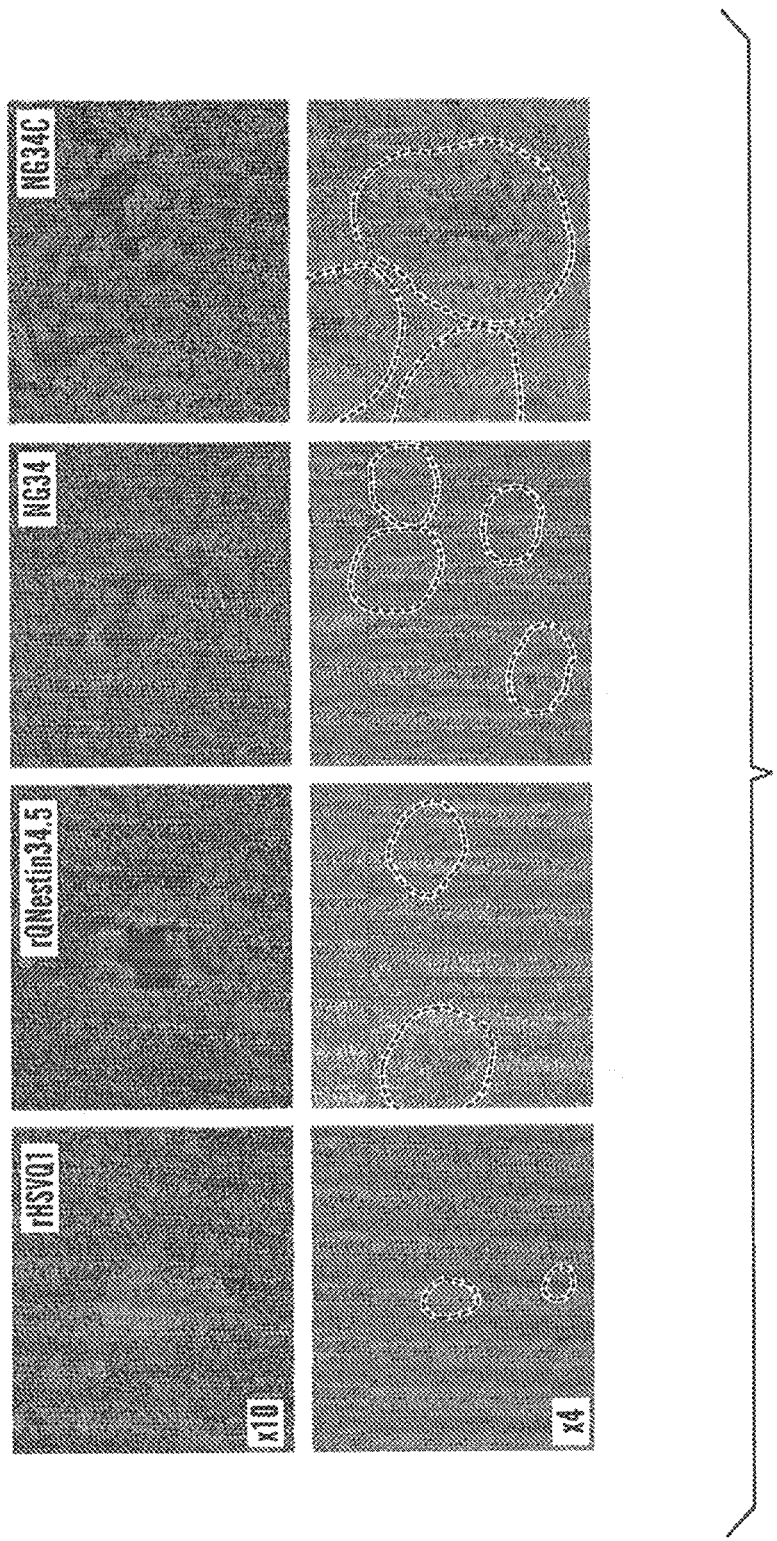
FIG. 6B demonstrates, in accordance with an embodiment of the invention, phase contrast microscopic images taken at 48 h post-infection to represent the plaque sizes of each oHSV1 in U251 cells.
Figure 7:
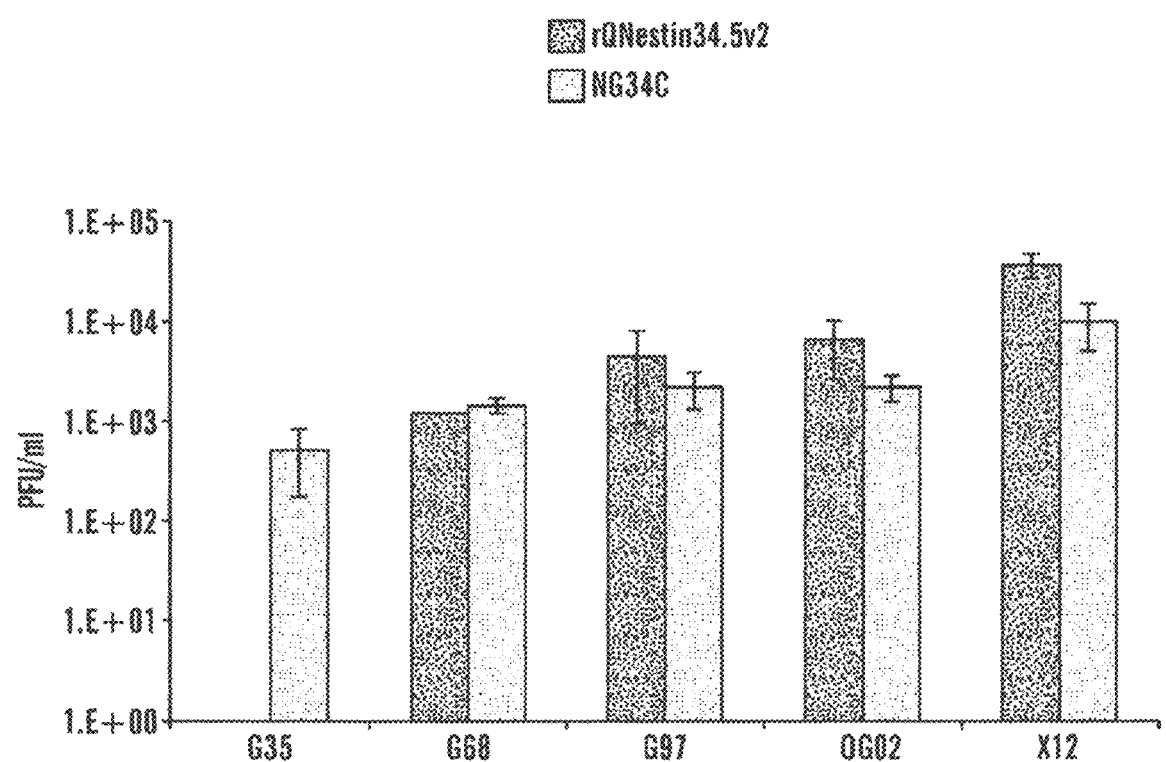
FIG. 7 demonstrates, in accordance with an embodiment of the invention, equivalent infectivity of NG34C as rQNestin34.5 in primary glioblastoma cells isolated form patients. rQNestin34.5 and NG34C were infected into 5 different GBMs cultured in serum-free Neurobasal media on PLL/laminin coated plates for three days, subsequent to the titration in Vero. N=3
Figure 8:
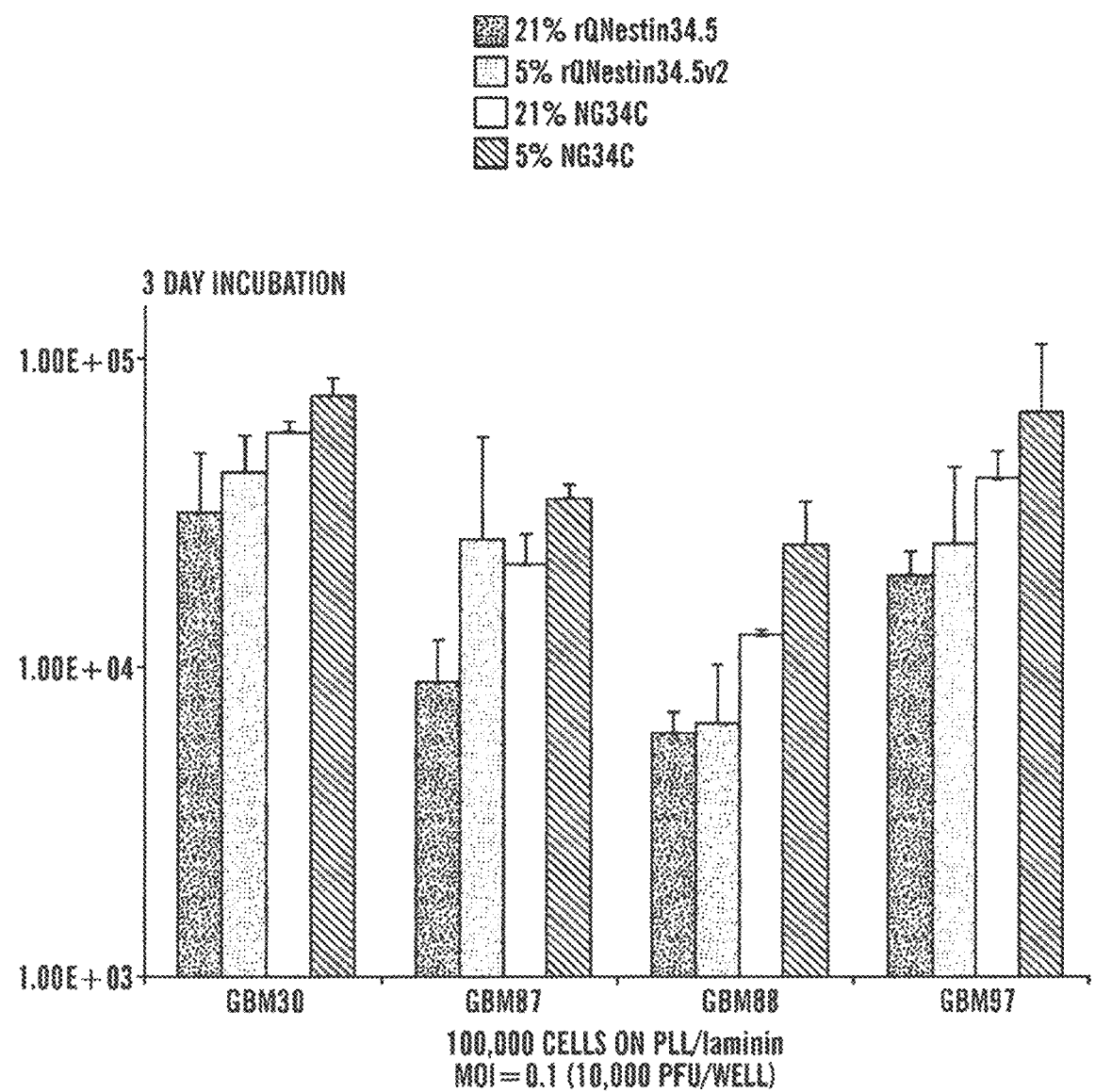
FIG. 8 demonstrates, in accordance with an embodiment of the invention, NG34C replicated more in lower oxygen condition cultured primary glioblastoma cells. rQNestin34.5 and NG34C at MOI of 0.1 were infected in 4 different GBMs cultured in serum-free Neurobasal media on PLL/laminin coated plates under normoxia (21% 02) or lower physiological oxygen condition (5% 02) for three days, subsequent to the titration in Vero. N=3
Figure 9:
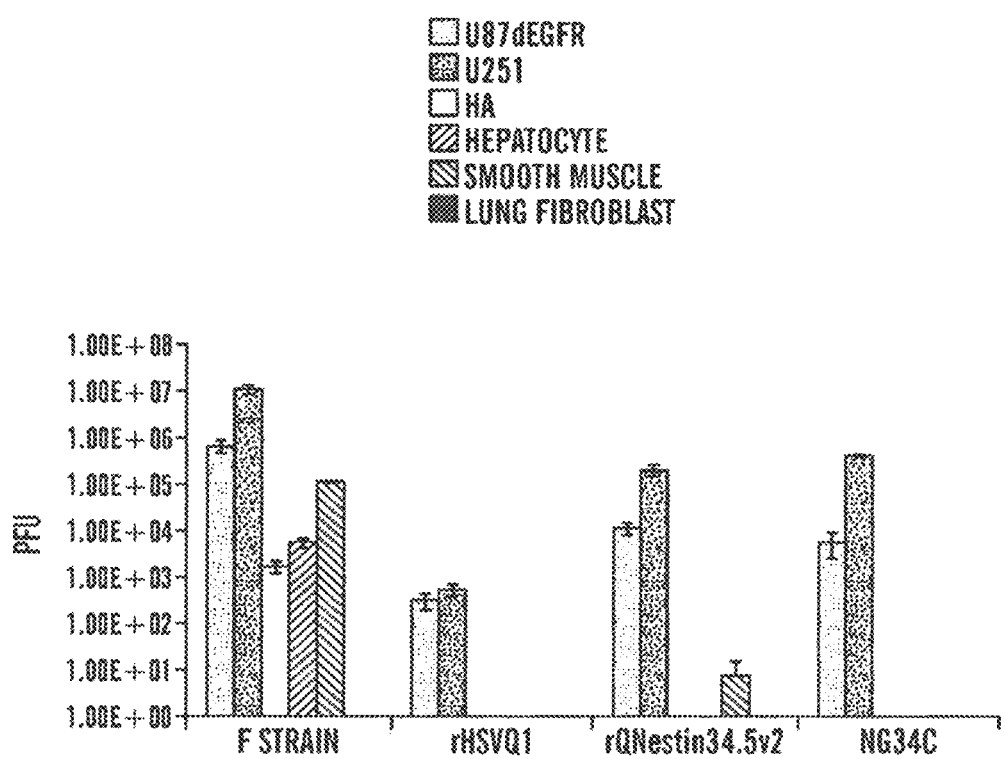
FIG. 9 demonstrates, in accordance with an embodiment of the invention, F strain-permissive primary normal tissue cells are resistant to NG34C infection. Glioma cell lines (U87dEGFR and U251), and primary human tissues (Astrocyte, Hepatocyte, Smooth Muscle and Lung fibroblast) were infected with wild-type HSV1 (F strain) and mutant HSV-1 (rHSVQ1, rQNestin34.5 and NG34C). These wild-type HSV1-permissive primary tissues didn't support the replication of mutant HSV1.
Figure 10:
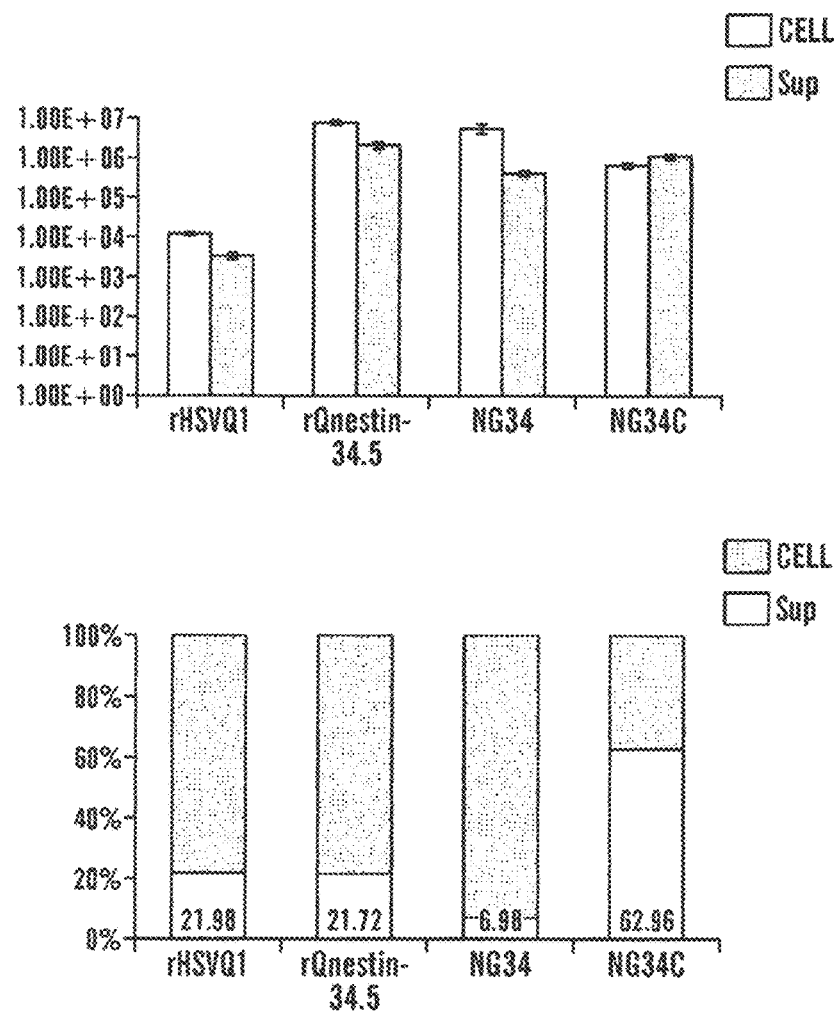
FIG. 10 demonstrates, in accordance with an embodiment of the invention, NG34C virus infected cells produced more progeny virus in medium (sup) than intracellular or on cellular membranes. Progeny virus yields were similar among rQNestin34.5, NG34 or NG34C, and 2-digits lower by rHSVQ1 virus as expected. However, NG34C progeny were higher in medium than in/on infected cells, while other oHSV1s were lower in medium, suggesting that NG34C is capable of more rapid distribution among cells than NG34 or rQNestin34.5 while total viral production doesn't change much between those oHSV1.
Figure 11:
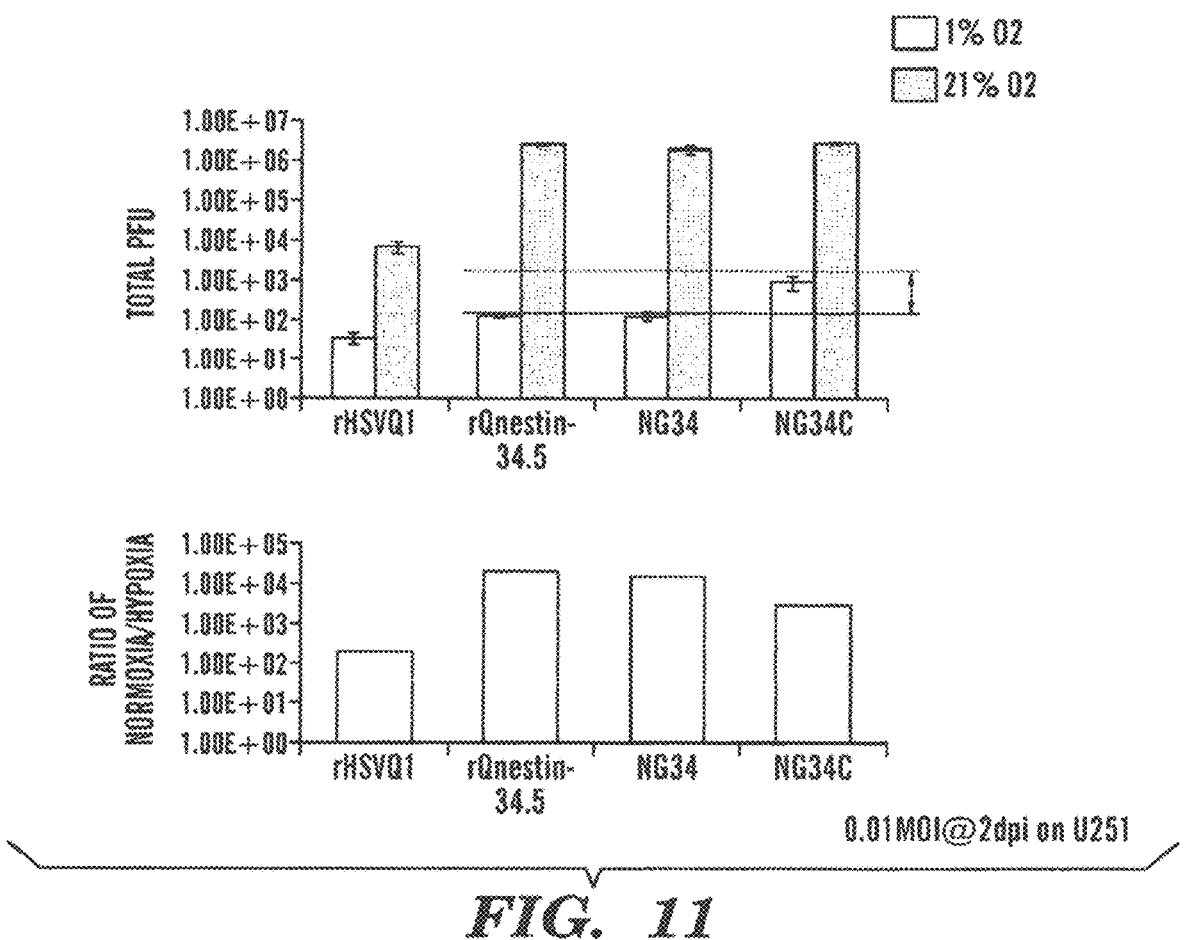
FIG. 11 demonstrates, in accordance with an embodiment of the invention, NG34C is more resistant to 1% hypoxia microenvironment, compared to rQNestin34.5 and NG34. Under severely lower oxygen conditions or hypoxia conditions (1% 02, 5% CO2 and 94% N2), oHSV1 replication was limited and the effect of ICP34.5 or GADD34 was not seen in rQNestin34.5 or NG34 infected U251 cells, when viral yields were compared to ICP34.5-null rHSVQ1 virus. In contrast, NG34C yields were still lower in hypoxia than that in normoxia (21%), but higher than other viruses.
Figure 12A:
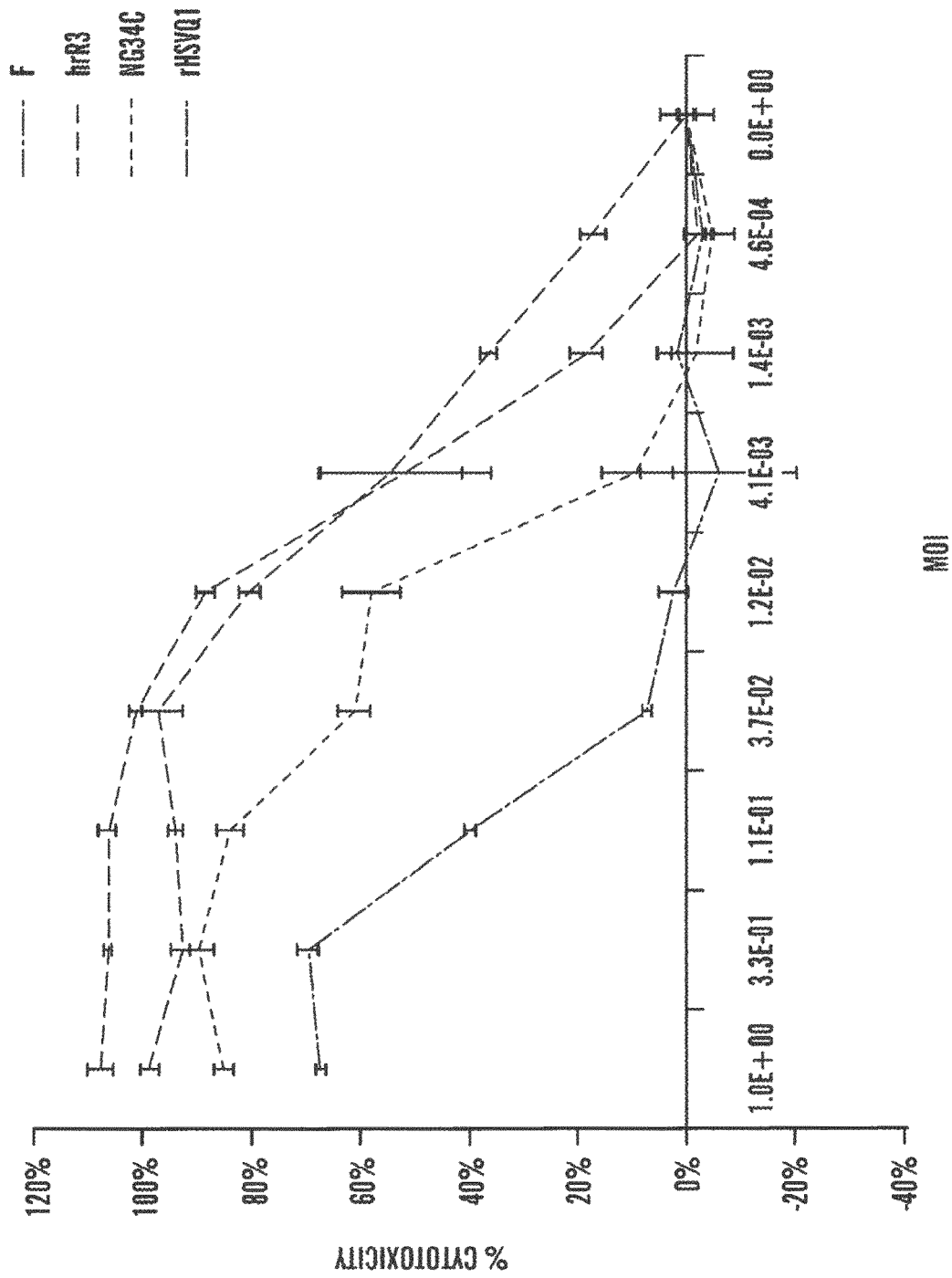
FIG. 12A demonstrates, in accordance with an embodiment of the invention, cytotoxicity of oHSV1 infection using U87ΔEGFR glioma cells. Serial dilutions of various HSV1 (F, hrR3, rHSVQ1, NG34C) from 0 to 1 PFU/cell were used to infected U87ΔdEGFR on a 96-well plate for 5 days before measuring quantitatively lactate dehydrogenase (LDH), a stable cytosolic enzyme that is released upon cell lysis, using CytoTox 96 cytotoxicity assay kit (Promega). N=4
Figure 12B:
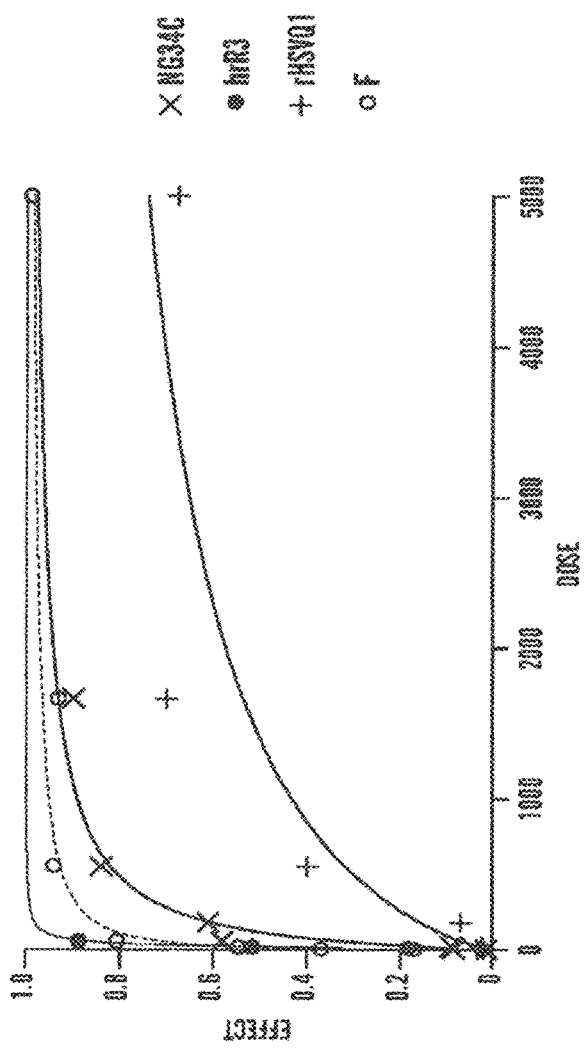
FIG. 12B data from panel (a) was plotted in the upper graph and median-effect dose (Dm) values (as MOI) were calculated in the table. m: a measurement of the sigmoidicity of the dose-effect curve, r: the linear correction coefficient of the median-effect plot.
Figure 13C:
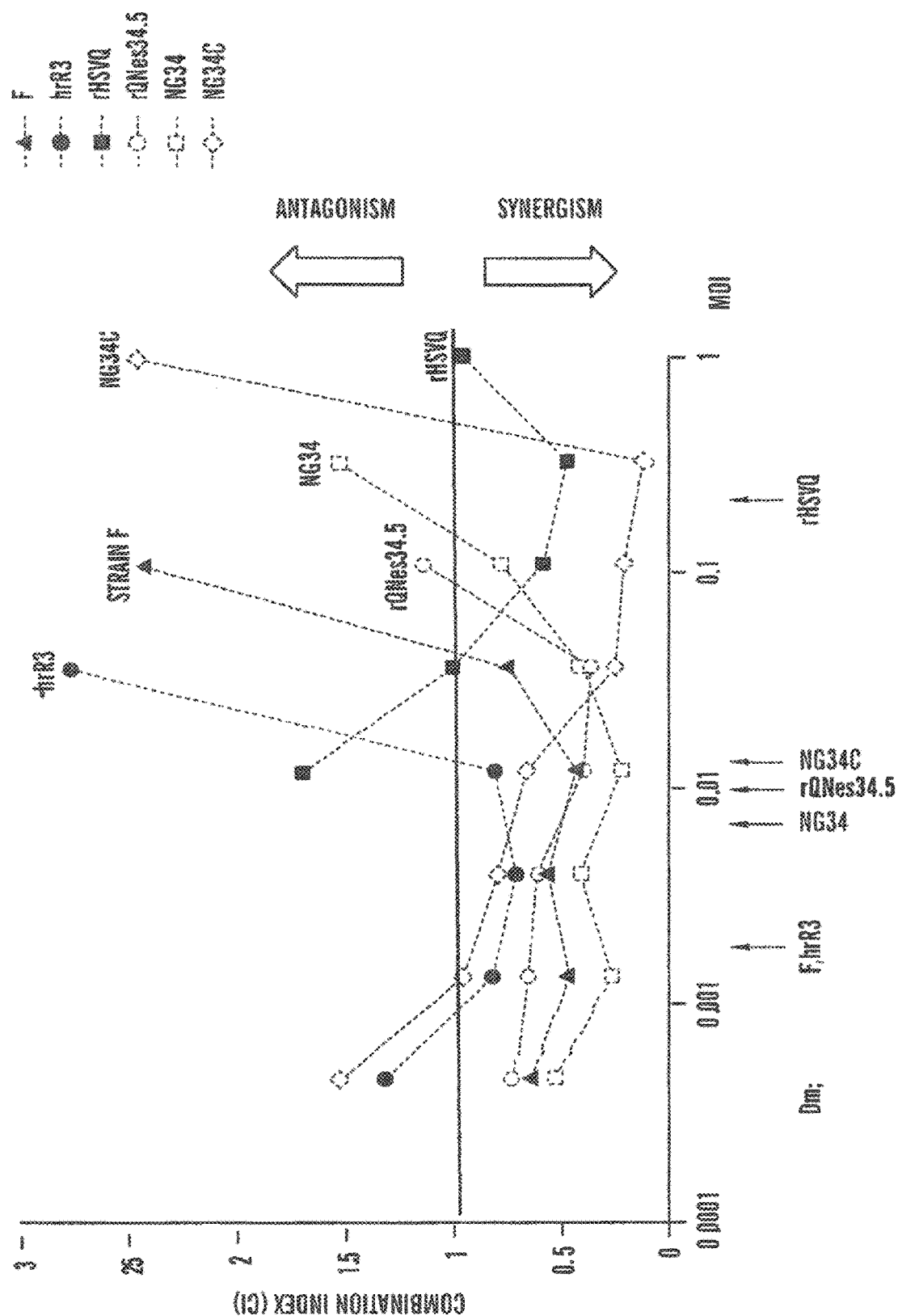
FIG. 13C demonstrates, in accordance with an embodiment of the invention, data from the tables of 13A and 13B were plotted. Less than 1 indicates synergism and more than 1 indicates antagonism. NG34 and rQNestin34.5 show more synergism at Dm values and NG34C showed more than Dm values. NG34, NG34C and rQNestin34.5 represented a broader range of synergistic effects with TMZ than rHSVQ or wild-type F or hrR3.
Figure 13D:
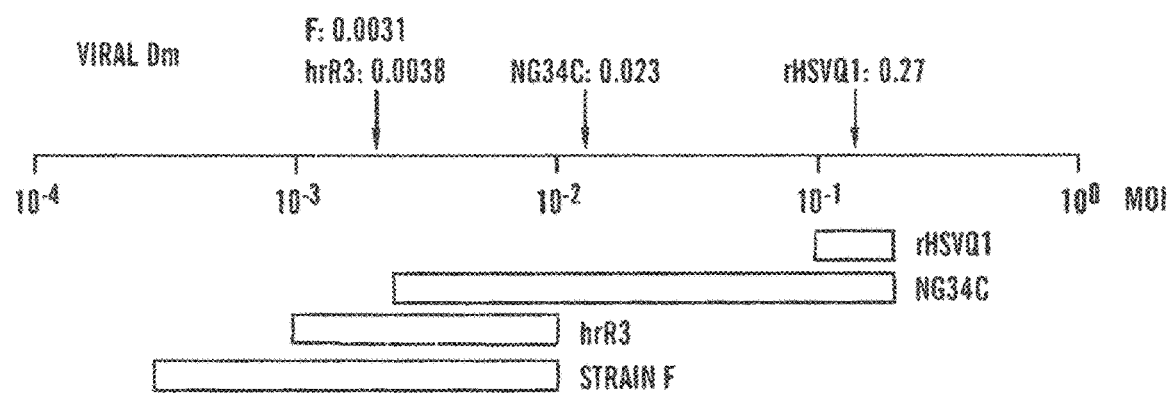
FIG. 13D demonstrates, in accordance with an embodiment of the invention, a graphic representation of the range of synergistic effects.

The HSVQuik method was employed to engineer HSV1 vectors as described herein and previously (see Terada et al. Development of a rapid method to generate multiple oncolytic HSV vectors and their in vivo evaluation using syngeneic mouse tumor models. Gene Ther_2006 April; 13(8): 705-14, which is incorporated herein by reference in its entirety). First, a full-length or N-terminal truncated GADD34 gene was inserted into the NcoI/HpaI sites of pTnestin-luc-b vector that inserts the nestin-hsp68 promoter-enhancer element into pTransfer, by ligating the fragment obtained by enzymatic digestion of blunt-ended BstXI/XhoI or HpaI/XhoI of a pOTB7-GADD34 (SEQ ID NO: 1) respectively (FIG. 3). These shuttle vectors were used to transform E. coli carrying the bacterial artificial chromosome (BAC) called fHsvQuik2, which has two flp recombination FRT sites within this UL39 locus, but lacks the EGFP gene from fHsvQuik1 (see Terada et al. Development of a rapid method to generate multiple oncolytic HSV vectors and their in vivo evaluation using syngeneic mouse tumor models. Gene Ther_2006 April; 13(8):705-14, which is incorporated herein by reference in its entirety). FLP-FRT mediated site-specific recombination between the shuttle vectors and fHsvQuik2 BAC resulted in fHsvQ2-nestin-GADD34 and fHsvQ2-nestin-GADD34ΔN BAC vectors, respectively (FIG. 4). Vero cells were transfected with these BACs and a pc-nCre, a Cre recombinase-expression vector to remove all the prokaryotic sequences from the shuttle vector flanking loxP sites. The resulting HSV1 viruses NG34 (containing full length GADD34) and NG34C (truncated GADD34) were generated and packaged in these Vero cells.

Example 2

Description of HSVQuik Vector System

The HsvQuik technology was developed as a novel BAC (bacterial artificial chromosome)-based method for the generation of oncolytic HSV-1. It takes advantage of relatively rapid and easy methods of conventional cloning by combining two sequential, site-specific recombination systems (Flp-FRT and Cre-loxP). The basic backbone for fHsvQuik vectors has been the genome of an oncolytic HSV-1 designated as MGH1, consisting of a double-mutant oncolytic HSV-1 (F strain) that has a lacZ gene insertional mutant UL39 (encoding a large subunit of ribonucleotide reductase, ICP6) and deletions of diploid $\gamma_1 34.5$ genes encoding the neurovirulence factor ICP34.5 responsible for encephalitis. To stably maintain this large HSV-1 genome in E. coli, the lacZ:UL39 locus of the MGH1 genome was also engineered to express additional genes encoding for the fluorescent markers, DsRed1 (for fHsvQuik-1 and −2) and EGFP (for fHsvQuik-1). The fHsvQuik BAC genome is not directly manipulated, rather its engineering with additional desired sequences is accomplished via a shuttle vector (pTransfer) that has been engineered with multiple cloning sites (MCSs) to insert gene(s) of interest with desired regulatory sequences (e.g. transcriptional regulatory elements). pTransfer contains an FRT site to allow direct site-specific integration into the fHsvQuik BAC DNA in Escherichia coli (E. coli) without enzymatic manipulation (e.g. DNA ligation). Because the R6Kγ replication origin of the pTransfer plasmid depends on E. coli strains that possess the pir gene, R6Kγ ori doesn't interfere with the bacterial replication origin of the fHsvQuik BAC in DH10B (pir) E. coli strains after Flp-FRT recombination. To remove the BAC sequences from the fHsvQuik DNA, the Cre-loxP recombination technique is used. The resultant recombinant HSV-1 clones forming individual plaques are distinguished from non-recombinant BAC-containing HSV-1 clones by RFP fluorescence since the CMV promoter-driving DsRed1 gene is also excised along with the BAC sequences during Cre-LoxP recombination.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of killing intracranial tumor cells in a subject, comprising introducing into the vicinity of the tumor cells an oncolytic expression vector, said oncolytic expression vector comprising a nucleic acid comprising a nucleotide sequence encoding GADD34 operably linked to an expression control sequence of SEQ ID NO: 3.

2. The method of claim 1, wherein the oncolytic expression vector is a modified herpes virus.

3. The method of claim 2, wherein the modified herpes virus is deficient for a γ134.5 gene.

4. The method of claim 1, wherein the nucleotide sequence comprises SEQ ID NO: 1.

5. The method of claim 1, wherein the nucleotide sequence comprises SEQ ID NO: 2.

6. The method of claim 1, further comprising the step of mixing a pharmacologically acceptable carrier with the oncolytic expression vector prior to the introducing step.

7. The method of claim 1, wherein the tumor cells comprise a glioblastoma cell or a cancer stem cell.

* * * * *